(12) United States Patent
Spada et al.

(10) Patent No.: US 9,861,576 B2
(45) Date of Patent: *Jan. 9, 2018

(54) BIODEGRADABLE ALPHA-2 AGONIST POLYMERIC IMPLANTS AND THERAPEUTIC USES THEREOF

(71) Applicant: Allergan, Inc., Irvine, CA (US)

(72) Inventors: Lon T. Spada, Walnut, CA (US); Alazar N. Ghebremeskel, Irvine, CA (US); Michael R. Robinson, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/383,079

(22) Filed: Dec. 19, 2016

(65) Prior Publication Data
US 2017/0100334 A1    Apr. 13, 2017

Related U.S. Application Data

(63) Continuation of application No. 14/816,401, filed on Aug. 3, 2015, now Pat. No. 9,522,113, which is a continuation of application No. 12/272,548, filed on Nov. 17, 2008, now Pat. No. 9,095,506.

(51) Int. Cl.
| | | |
|---|---|---|
| *A61K 9/00* | (2006.01) | |
| *A61K 31/498* | (2006.01) | |
| *A61K 47/34* | (2017.01) | |

(52) U.S. Cl.
CPC .......... *A61K 9/0051* (2013.01); *A61K 31/498* (2013.01); *A61K 47/34* (2013.01)

(58) Field of Classification Search
CPC .................................................. A61K 9/0051
See application file for complete search history.

(56) References Cited

U.S. PATENT DOCUMENTS

| | | |
|---|---|---|
| 4,327,725 A | 5/1982 | Cortese |
| 4,474,451 A | 10/1984 | Mizokami |
| 4,521,210 A | 6/1985 | Wong |

(Continued)

FOREIGN PATENT DOCUMENTS

| | | |
|---|---|---|
| CA | 2294714 | 1/1999 |
| EP | 0488401 | 6/1992 |

(Continued)

OTHER PUBLICATIONS

Asbell, Penny et al, Effects of Topical Antiglaucoma Medications on the Ocular Surface, The Ocular Surface, 2005, 27-40, 1.

(Continued)

*Primary Examiner* — Benjamin Packard
(74) *Attorney, Agent, or Firm* — Laura L. Wine

(57) ABSTRACT

Biocompatible intraocular implants include an alpha-2 adrenergic receptor agonist and a polymer associated with the alpha-2 adrenergic receptor agonist to facilitate release of the alpha-2 adrenergic receptor agonist into an eye for an extended period of time. The alpha-2 adrenergic receptor agonist may be associated with a biodegradable polymer matrix, such as a matrix of a two biodegradable polymers. The implants can be placed in an eye to treat one or more ocular conditions, such as an ocular vasculopathy or glaucoma, including reduction of an elevated intraocular pressure.

5 Claims, 4 Drawing Sheets

Release Profiles for BFB and BT Containing Formulations

(56) References Cited

U.S. PATENT DOCUMENTS

| | | | |
|---|---|---|---|
| 4,853,224 | A | 8/1989 | Wong |
| 4,997,652 | A | 3/1991 | Wong |
| 5,164,188 | A | 11/1992 | Wong |
| 5,264,188 | A | 11/1993 | Lew |
| 5,443,505 | A | 8/1995 | Wong et al. |
| 5,501,856 | A | 3/1996 | Ohtori et al. |
| 5,766,242 | A | 6/1998 | Wong et al. |
| 5,824,072 | A | 10/1998 | Wong |
| 5,856,329 | A | 1/1999 | Wheeler et al. |
| 5,869,079 | A | 2/1999 | Wong et al. |
| 6,066,675 | A | 5/2000 | Wen et al. |
| 6,074,661 | A | 6/2000 | Olejnik et al. |
| 6,194,415 | B1 | 2/2001 | Wheeler et al. |
| 6,248,741 | B1 | 6/2001 | Wheeler et al. |
| 6,309,669 | B1 | 10/2001 | Setterstrom et al. |
| 6,331,313 | B1 | 12/2001 | Wong et al. |
| 6,369,116 | B1 | 4/2002 | Wong et al. |
| 6,413,245 | B1 | 7/2002 | Yaacobi et al. |
| 6,465,464 | B2 | 10/2002 | Wheeler et al. |
| 6,692,759 | B1 | 2/2004 | Wong et al. |
| 6,699,493 | B2 | 3/2004 | Wong |
| 8,293,210 | B2 | 10/2012 | Huang et al. |
| 8,293,741 | B2 | 10/2012 | Burke et al. |
| 2001/0049369 | A1* | 12/2001 | Jablonski ............. A61K 31/498 514/250 |
| 2003/0157178 | A1 | 8/2003 | Chen et al. |
| 2004/0001889 | A1 | 1/2004 | Chen |
| 2004/0013704 | A1 | 1/2004 | Kabra et al. |
| 2004/0054374 | A1 | 3/2004 | Weber et al. |
| 2004/0151753 | A1 | 8/2004 | Chen et al. |
| 2005/0244506 | A1 | 10/2005 | Burke et al. |
| 2005/0244458 | A1 | 11/2005 | Huang et al. |
| 2005/0244463 | A1 | 11/2005 | Huang |
| 2005/0244464 | A1 | 11/2005 | Hughes |
| 2005/0244471 | A1 | 11/2005 | Shiah et al. |
| 2005/0244476 | A1 | 11/2005 | Burke et al. |
| 2005/0244479 | A1 | 11/2005 | Huang et al. |
| 2006/0182781 | A1 | 8/2006 | Hughes |
| 2006/0233860 | A1 | 10/2006 | Chang et al. |
| 2008/0118547 | A1 | 5/2008 | Huang et al. |
| 2008/0118548 | A1 | 5/2008 | Huang et al. |
| 2008/0118549 | A1 | 5/2008 | Huang et al. |
| 2008/0131372 | A1 | 6/2008 | Huang et al. |
| 2008/0131485 | A1 | 6/2008 | Huang et al. |
| 2008/0260832 | A1 | 10/2008 | Burke et al. |
| 2008/0299178 | A1 | 12/2008 | Burke et al. |
| 2011/0251201 | A1 | 10/2011 | Huang et al. |

FOREIGN PATENT DOCUMENTS

| | | |
|---|---|---|
| EP | 0992244 A4 | 1/2001 |
| WO | 2002-36162 A2 | 5/2002 |
| WO | 2003-077952 | 9/2003 |
| WO | 2004032934 A1 | 4/2004 |
| WO | 2004-066979 | 8/2004 |
| WO | 2005-110367 | 11/2005 |
| WO | 2005-110368 | 11/2005 |
| WO | 2006-122165 | 11/2006 |
| WO | 2007-150018 | 12/2007 |
| WO | 2007-150018 A2 | 12/2007 |
| WO | 2008-070402 | 6/2008 |

OTHER PUBLICATIONS

Bartlett, J.D. et al, Contrast Sensitivity Improvements in Brimonidine-Treated Primary Open-Angle Glaucoma Patients Suggest a Neuroprotective Mechanism, ARVO Meeting, 2002, 1 Page, Biosis.

De Jong, S.J. et al, New insights into the hydrolytic degradation of poly(lactic acid): participation of the alcohol terminus, Polymer, 2001, 2795-2802, 42.

Del Amo, Eva et al, Current and Future Ophthalmic Drug Delivery Systems: A Shift to the Posterior Segment, Drug Discovery Today, Feb. 2008, 135-143, 13 (3/4).

Heller, Jorge, Biodegradable Polymers in Controlled Drug Delivery, CRC Critical Reviews in Therapeutic Drug carrier Systems, 1987, 39-90, 1(1).

Lee, Susan et al, Biodegradable Implants for Sustained Drug Release in the Eye, Pharm Res, 2010, 2043-2053, 27.

Lewis, Danny, Controlled Release of Bioactive Agents from Lactide/Glycolide Polymers, Biodegradable Polymers as Drug Delivery Systems, 1990, 1-35, 45.

M.A. Tracy, et al., Effects of PLGA End Groups on Degradation, Proceed. Intern. Symp. Control. Rel. Bloact Mater.,, 1995, 786-787, 22, US.

Merkli, Alain et al, Use of Insoluble Biodegradable Polymers in Ophthalmic Systems for the Sustained Release of Drugs, European Journal of Pharmaceutics and Biopharmaceutics, 1995, 271-283, 41 (5), US.

Mueller, M., Tear Film Break Up Time and Schirmer Test After Different Antiglaucomatous Medications, Invest Ophthalmol Vis Sci, Mar. 15, 2000, S283, vol. 41.

Notification of Transmittal of the International Search Rep[ort and the Written Opinion of the International Searching Authority, International Application No. PCT/US2009/063490, International Filing Date Nov. 6, 2009, dated Nov. 8, 2009.

Raymond Rowe et al, Handbook of Pharmaceutical Excipients, APha Publications, 2003, 2 pages, 4th edition.

Sigma Aldrich, Poly(D,L-lactide-co-glycolide) acid terminated, Mw 7,000-17,000/, Sigma Aldrich, Sep. 19, 2014, XP055141404.

U.S. Appl. No. 10/837,143, filed Apr. 30, 2004.
U.S. Appl. No. 11/118,519, filed Apr. 29, 2005.
U.S. Appl. No. 11/303,462, filed Dec. 15, 2005.
U.S. Appl. No. 11/371,118, filed Mar. 8, 2006.
U.S. Appl. No. 11/395,019, filed Mar. 31, 2006.
U.S. Appl. No. 11/565,917, filed Dec. 1, 2006.
U.S. Appl. No. 10/836,911, filed Apr. 30, 2004.
U.S. Appl. No. 11/119,021, filed Apr. 29, 2005.
U.S. Appl. No. 12/024,017, filed Jan. 31, 2008.
U.S. Appl. No. 09/998,718, filed Nov. 1, 2001.
U.S. Appl. No. 10/020,541, filed Apr. 26, 2002.

United States Board of Patent Appeals and Interferences decision on appeal in Ex parte Hughes et al, Appeal No. 2010-004999, U.S. Appl. No. 10/836,911, mailed Oct. 25, 2010.

United States Pharmacopeia, The National Formulary, USP23, 1995, 1790-1798, 18.

Urtti, Arto, et al., Controlled Drug Delivery Devices for Experimental Ocular Studies with Timolol 2. Ocular and Systemic Absorption in Rabbits, International Journal of Pharmaceutics, 1990, 241-249, vol. 61, Elsevier.

U.S. Appl. No. 11/394,765, filed Mar. 31, 2006.
U.S. Appl. No. 11/927,613, filed Oct. 29, 2007.
U.S. Appl. No. 11/927,615, filed Oct. 29, 2007.
U.S. Appl. No. 12/024,010, filed Jan. 31, 2008.
U.S. Appl. No. 12/024,014, filed Jan. 31, 2008.

Yasukawa, T. et al., Biodegradable Scleral Plugs for Vitreoretinal Drug Delivery, Advanced Drug Delivery Reviews, 2001, 25-36, 52, US.

* cited by examiner

Figure 1. Release Profiles for BFB and BT Containing Formulations
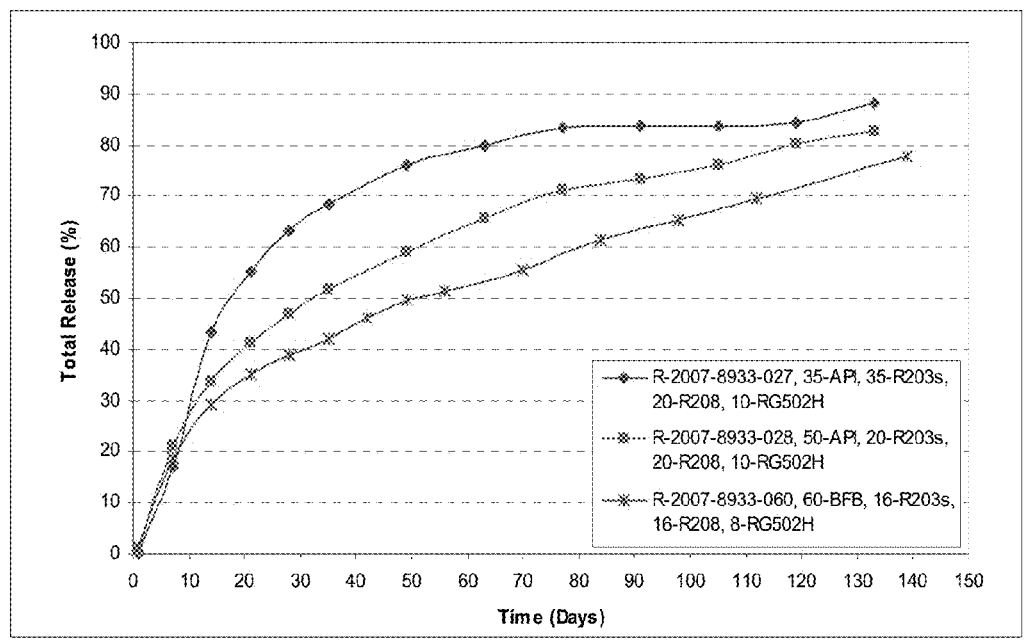

Figure 2. Release Profiles for BFB and BT Containing Formulations

Figure 3 (a) Bar-shaped polymer implant and (b) Disc-shaped polymer implant

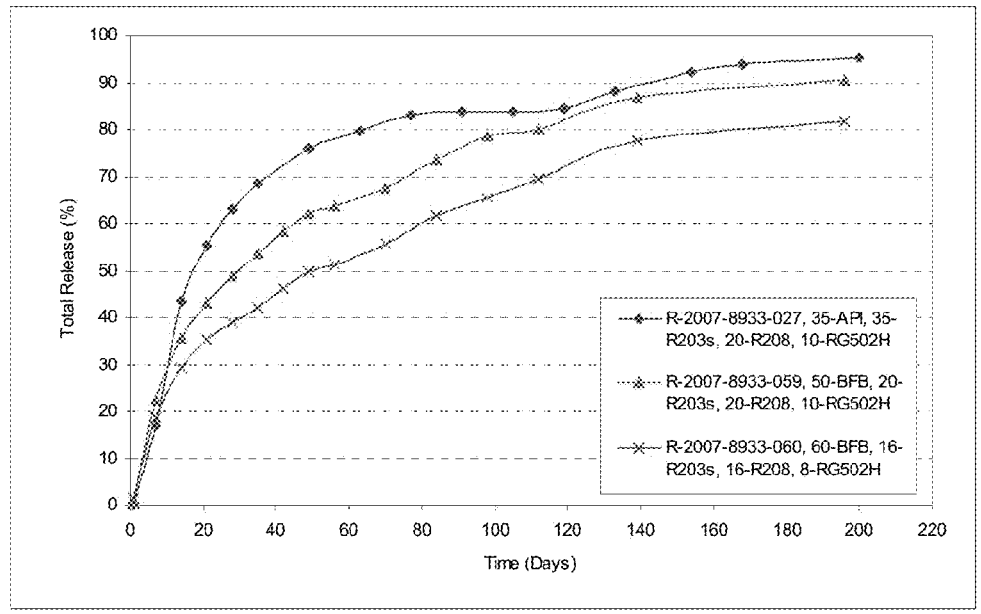
Figure 4. Release profiles for BFB containing formulations made by melt extrusion (bars)
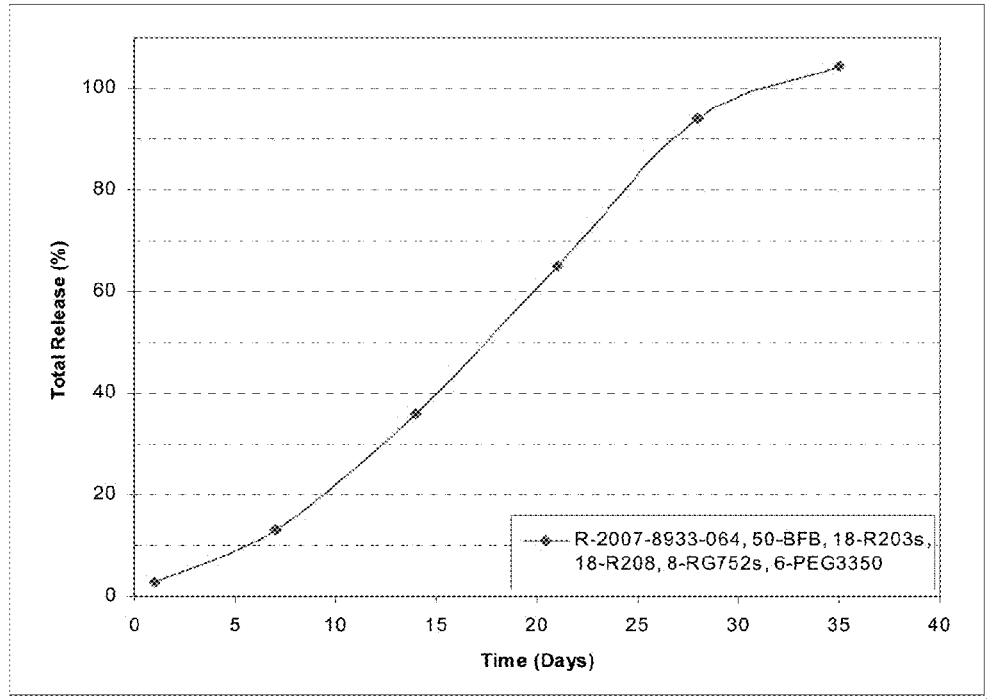
Figure 5. Release profiles for BFB containing formulation made by injection molding (disc)

Figure 6. Percent Change in IOP from Baseline Observed in Rabbit Eyes Dosed with Brimonidine Tartrate Bars (2400 μg brimonidine tartrate)
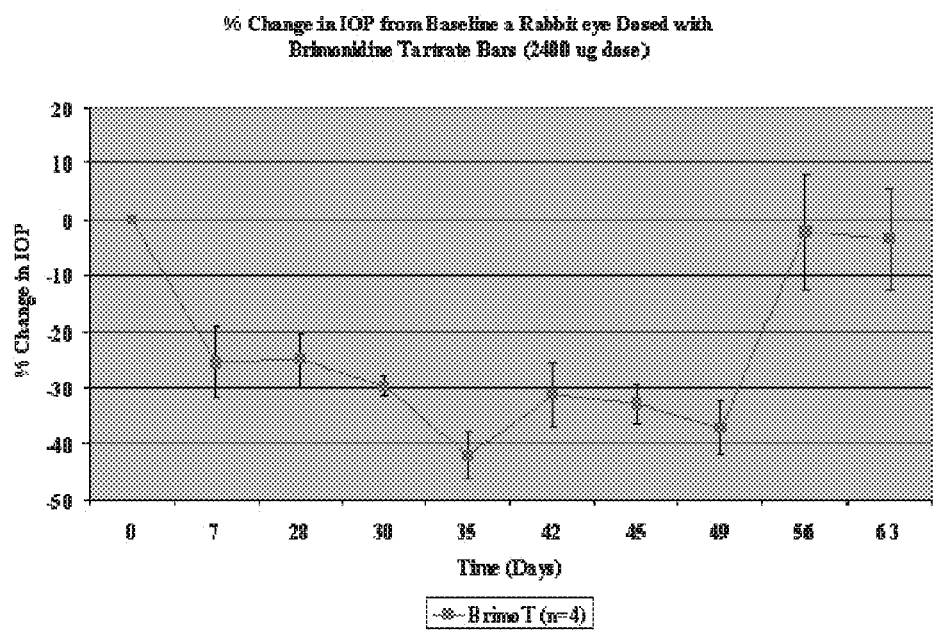

BIODEGRADABLE ALPHA-2 AGONIST POLYMERIC IMPLANTS AND THERAPEUTIC USES THEREOF

CROSS-REFERENCE

This application is a continuation of copending U.S. patent application Ser. No. 14/816,401, filed on Aug. 3, 2015, which is a continuation of U.S. patent application Ser. No. 12/272,548, filed on Nov. 17, 2008, now issued as U.S. Pat. No. 9,095,506, the entire disclosure of both applications is incorporated herein by this specific reference.

BACKGROUND

The present invention relates to bioerodible, sustained release intraocular implants and methods for treating an ocular disease or condition. Brimonidine (5-bromo-6-(2-imidazolidinylideneamino)quinoxaline) is an alpha-2-selective adrenergic receptor agonist effective for treating open-angle glaucoma by decreasing aqueous humor production and increasing uveoscleral outflow. Brimonidine is available in at least two chemical forms, brimonidine tartrate and brimonidine free base. Topical ocular brimonidine tartrate formulation, 0.15% Alphagan P® (Allergan, Irvine, Calif.), has been used to treat of open-angle glaucoma. The solubility of brimonidine tartrate in water is 34 mg/mL, while the solubility of brimonidine freebase is negligible in water. Topical formulations of brimonidine to treat glaucoma are administered daily. Hence, it would be advantageous to have a sustained release formulation of an alpha-2-selective adrenergic receptor agonist, such as brimonidine, which can be administered (i.e. by intrascleral injection or implantation of a suitable implant) once every one to six months to provide regular dosing of the alpha-2-selective adrenergic receptor agonist therapeutic agent to the eye of a patient in need thereof to thereby treat an ocular condition such as the elevated intraocular pressure characteristic of glaucoma.

Recent studies have suggested that brimonidine can also promote survival of injured retinal ganglion nerve cells by activation of the alpha-2-adrenoceptor in the retina and/or optic nerve. For example, brimonidine can protect injured neurons from further damage in several models of ischemia and glaucoma. See e.g. U.S. Pat. Nos. 5,856,329; 6,194,415; 6,248,741, and; 6,465,464.

Glaucoma-induced retinal ganglion cell degeneration (neurodegeneration) is one of the leading causes of blindness. This indicates that brimonidine can be utilized in glaucoma management in which neuroprotection (through mitigation of neurodegeneration) and/or intraocular pressure reduction are valued outcomes of the therapeutic regimen. For brimonidine to protect the optic nerve, however, it must have access to the posterior segment of the eye at therapeutic levels. Hence, it would be advantageous to have a sustained release formulation of an alpha-2-selective adrenergic receptor agonist, such as brimonidine, which can be administered (i.e. by intravitreal injection or implantation of a suitable implant) once every one to six months to provide regular dosing of the alpha-2-selective adrenergic receptor agonist therapeutic agent to the eye of a patient in need thereof to thereby treat an ocular condition such as neurodegeneration another retinal disorder or condition such as macular degeneration, macular edema or other retinopathy.

Macular degeneration, such as age related macular degeneration ("AMD") is a leading cause of blindness in the world. It is estimated that thirteen million Americans have evidence of macular degeneration. Macular degeneration results in a break down the macula, the light-sensitive part of the retina responsible for the sharp, direct vision needed to read or drive. Central vision is especially affected. Macular degeneration is diagnosed as either dry (atrophic) or wet (exudative). The dry form of macular degeneration is more common than the wet form of macular degeneration, with about 90% of AMD patients being diagnosed with dry AMD. The wet form of the disease usually leads to more serious vision loss. Macular degeneration can produce a slow or sudden painless loss of vision. The cause of macular degeneration is not clear. The dry form of AMD may result from the aging and thinning of macular tissues, depositing of pigment in the macula, or a combination of the two processes. With wet AMD, new blood vessels grow beneath the retina and leak blood and fluid. This leakage causes retinal cells to die and creates blind spots in central vision.

Macular edema ("ME") can result in a swelling of the macula. The edema is caused by fluid leaking from retinal blood vessels. Blood leaks out of the weak vessel walls into a very small area of the macula which is rich in cones, the nerve endings that detect color and from which daytime vision depends. Blurring then occurs in the middle or just to the side of the central visual field. Visual loss can progress over a period of months. Retinal blood vessel obstruction, eye inflammation, and age-related macular degeneration have all been associated with macular edema. The macula may also be affected by swelling following cataract extraction. Symptoms of ME include blurred central vision, distorted vision, vision tinted pink and light sensitivity. Causes of ME can include retinal vein occlusion, macular degeneration, diabetic macular leakage, eye inflammation, idiopathic central serous chorioretinopathy, anterior or posterior uveitis, pars planitis, retinitis pigmentosa, radiation retinopathy, posterior vitreous detachment, epiretinal membrane formation, idiopathic juxtafoveal retinal telangiectasia, Nd:YAG capsulotomy or iridotomy. Some patients with ME may have a history of use of topical epinephrine or prostaglandin analogs for glaucoma. The first line of treatment for ME is typically anti-inflammatory drops topically applied.

Diabetic retinopathy is the leading cause of blindness among adults aged 20 to 74 years. Macular ischemia is a major cause of irreversible vision acuity loss and decreased contrast sensitivity in patients with diabetic retinopathy. The capillary nonperfusion and decreased capillary blood flow that is responsible for this ischemia is seen clinically on the fluorescein angiogram as an increase in the foveal avascular zone (FAZ) or an irregularity of the outline of the FAZ. These findings are predictors of the other, perhaps more well-known, sight-threatening complications of diabetic retinopathy, including macular edema and proliferative retinopathy. Perhaps more importantly, extensive capillary nonperfusion is also a predictor of a poor visual prognosis from diabetic retinopathy.

The exterior surface of the normal globe mammalian eye has a layer of tissue known as conjunctival epithelium, under which is a layer of tissue called Tenon's fascia (also called conjunctival stroma). The extent of the Tenon's fascia extending backwards across the globe forms a fascial sheath known as Tenon's capsule. Under Tenon's fascia is the episclera. Collectively, the conjunctival epithelium and the Tenon's fascia is referred to as the conjunctiva. As noted, under Tenon's fascia is the episclera, underneath which lies the sclera, followed by the choroid. Most of the lymphatic vessels and their associated drainage system, which is very efficient at removing therapeutic agents placed in their vicinity, is present in the conjunctiva of the eye.

A therapeutic agent can be administered to the eye to treat an ocular condition. For example the target tissue for an antihypertensive therapeutic agent to treat the elevated intraocular pressure characteristic of glaucoma can be the ciliary body and/or the trabecular meshwork. Unfortunately, administration of an ocular topical antihypertensive pharmaceutical in the form of eye drops can result in a rapid wash out of most if not all of the therapeutic agent before it reaches the ciliary body and/or the trabecular meshwork target tissue, thereby requiring frequent redosing to effectively treat a hypertensive condition. Additionally, side effects to patients from topical administration of antiglaucoma medications and their preservatives range from ocular discomfort to sight-threatening alterations of the ocular surface, including conjunctival hyperemia (eye redness), stinging, pain, decreased tear production and function, decreased tear film stability, superficial punctate keratitis, squamous cell metaplasia, and changes in cell morphology. These adverse effects of topical antiglaucoma eyedrops can interfere with the treatment of glaucoma by discouraging patient dosing compliance, and as well long-term treatment with eyedrops is associated with a higher failure of filtration surgery. Asbell P. A., et al *Effects of topical antiglaucoma medications on the ocular surface*, Ocul Surf 2005 January; 3 (1):27-40; Mueller M., et al. *Tear film break up time and Schirmer test after different antiglaucomatous medications*, Invest Ophthalmol Vis Sci 2000 Mar. 15; 41 (4):5283. Thus it would be advantageous to have an intraocular, sustained release formulation of an alpha-2 agonist for treating glaucoma which does not have the side effects rapid drug wash out, ocular discomfort, conjunctival hyperemia (eye redness), stinging, pain, decreased tear production and function, decreased tear film stability, superficial punctate keratitis, squamous cell metaplasia, and changes in cell morphology.

It is known to administer a drug depot to the posterior (i.e. near the macula) sub-Tenon space. See eg column 4 of U.S. Pat. No. 6,413,245. Additionally, it is known to administer a polylactic implant to the sub-tenon space or to a suprachoroidal location. See eg published U.S. Pat. No. 5,264,188 and published U.S. patent application 20050244463.

Drug delivery systems have been formulated with various active agents. For example, it is known to make 2-methoxyestradiol poly lactic acid polymer implants (as rods and wafers), intended for intraocular use, by a melt extrusion method. See eg published U.S. patent application 20050244471. Additionally, it is known to make brimonidine poly lactic acid polymer implants and microspheres intended for intraocular use. See eg published U.S. patent applications 20050244463 and 20050244506, and U.S. patent application Ser. No. 11/395,019. Furthermore, it is known to make bimatoprost containing polylactic acid polymer implants and microspheres intended for intraocular use. See eg published U.S. patent applications 2005 0244464 and 2006 0182781, and U.S. patent application Ser. No. 11/303, 462, and; Ser. No. 11/371,118.

Brimonidine is an $\alpha_{2B}$-selective adrenergic agonist used to treat open-angle glaucoma by decreasing aqueous humor production and increasing uveoscleral outflow. The chemical structure of brimonidine tartrate is:

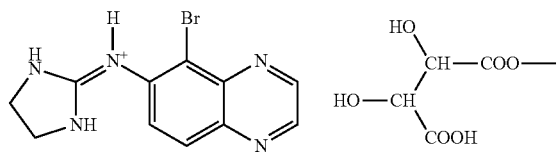

The chemical formula for brimonidine tartrate is F, 5-bromo-6-(2-imidazolidinylideneamino)quinoxaline tartrate $C_{15}H_{16}N_5O_6Br$ or $(C_{11}H_{10}BrN_5 \cdot C_4H_6O_6)$ Brimonidine tartrate has been used in ophthalmic solutions in concentrations of 0.2%, 0.15% and 0.1%. It has been suggested that brimonidine can have a neuroprotective effect upon retinal cells. See eg U.S. Pat. Nos. 5,856,329; 6,194, 415; 6,248,741, and; 6,465,464.

Biocompatible implants for placement in the eye have been disclosed in a number of patents, such as U.S. Pat. Nos. 4,521,210; 4,853,224; 4,997,652; 5,164,188; 5,443,505; 5,501,856; 5,766,242; 5,824,072; 5,869,079; 6,074,661; 6,331,313; 6,369,116; 6,066,675, and 6,699,493. Relevant U.S. patent applications include Ser. Nos. 10/020,541; 09/998,718; 10/836,911; 11/119,021; 11/394,765; 12/024, 010; 12/024,014; 12/024,017; 10/837,143; 11/118,519; 11/927,613; 11/927,615; 11/395,019, and Ser. No. 11/565, 917.

It would be advantageous to provide eye implantable drug delivery systems, such as intraocular implants, and methods of using such systems, that are capable of releasing a therapeutic agent at a sustained or controlled rate for extended periods of time and in amounts with few or no negative side effects to treat an ocular disease or condition such as glaucoma, neurodegeneration, or a retinal disorder or condition.

SUMMARY

The present invention meets this need and provides new drug delivery systems, and methods of making and using such systems for extended or sustained drug release into an eye to treat an ocular disease or condition. Our drug delivery systems are in the form of intraocular implants. The present systems and methods advantageously provide for extended release times of one or more therapeutic agents. Thus, the patient in whose eye the implant has been placed receives a therapeutic amount of an agent for a long or extended time period without requiring additional administrations of the agent. Thus, the patient has a substantially consistent level of therapeutically active agent available for consistent treatment of the eye over a relatively long period of time, for example, on the order of at least about one week, such as between about two and about six months after receiving an implant. Such extended release times facilitate obtaining successful treatment results.

Definitions

As use herein the terms below have the meanings set forth.

"About" means plus or minus ten percent of the value, parameter or characteristic so qualified.

"Biocompatible" means that there is an insignificant inflammatory response upon contact of the biocompatible material with an ocular tissue.

"Effective amount" as applied to an active agent means that amount of the compound which is generally sufficient to effect a desired change in the subject.

"Intraocular implant" means a device or element that is structured, sized, or otherwise configured to be placed in an eye. Intraocular implants are generally biocompatible with physiological conditions of an eye and do not cause adverse side effects. Intraocular implants may be placed in an eye without disrupting vision of the eye.

"Therapeutic component" means a portion of an intraocular implant comprising one or more therapeutic agents or substances used to treat a medical condition of the eye. The therapeutic component may be a discrete region of an intraocular implant, or it may be homogenously distributed throughout the implant. The therapeutic agents of the therapeutic component are typically ophthalmically acceptable, and are provided in a form that does not cause adverse reactions when the implant is placed in an eye.

"Drug release sustaining component" means a portion of the intraocular implant that is effective to provide a sustained release of the therapeutic agents of the implant. A drug release sustaining component may be a biodegradable polymer matrix, or it may be a coating covering a core region of the implant that comprises a therapeutic component.

"Associated with" means mixed with, dispersed within, coupled to, covering, or surrounding.

"Ocular region" or "ocular site" means any area of the eyeball, including the anterior and posterior segment of the eye, and which generally includes, but is not limited to, any functional (e.g., for vision) or structural tissues found in the eyeball, or tissues or cellular layers that partly or completely line the interior or exterior of the eyeball. Specific examples of areas of the eyeball in an ocular region include the anterior chamber, the posterior chamber, the vitreous cavity, the choroid, the suprachoroidal space, the conjunctiva, the subconjunctival space, the episcleral space, the intracorneal space, the epicorneal space, the sclera, the pars plana, surgically-induced avascular regions, the macula, and the retina.

"Ocular condition" means a disease, ailment or condition which affects or involves the eye or one of the parts or regions of the eye. Broadly speaking the eye includes the eyeball and the tissues and fluids which constitute the eyeball, the periocular muscles (such as the oblique and rectus muscles) and the portion of the optic nerve which is within or adjacent to the eyeball.

An anterior ocular condition is a disease, ailment or condition which affects or which involves an anterior (i.e. front of the eye) ocular region or site, such as a periocular muscle, an eye lid or an eye ball tissue or fluid which is located anterior to the posterior wall of the lens capsule or ciliary muscles. Thus, an anterior ocular condition primarily affects or involves the conjunctiva, the cornea, the anterior chamber, the iris, the posterior chamber (behind the retina but in front of the posterior wall of the lens capsule), the lens or the lens capsule and blood vessels and nerve which vascularize or innervate an anterior ocular region or site.

Thus, an anterior ocular condition can include a disease, ailment or condition, such as for example, aphakia; pseudophakia; astigmatism; blepharospasm; cataract; conjunctival diseases; conjunctivitis; corneal diseases; corneal ulcer; dry eye syndromes; eyelid diseases; lacrimal apparatus diseases; lacrimal duct obstruction; myopia; presbyopia; pupil disorders; refractive disorders and strabismus. Glaucoma can also be considered to be an anterior ocular condition because a clinical goal of glaucoma treatment can be to reduce a hypertension of aqueous fluid in the anterior chamber of the eye (i.e. reduce intraocular pressure).

A posterior ocular condition is a disease, ailment or condition which primarily affects or involves a posterior ocular region or site such as choroid or sclera (in a position posterior to a plane through the posterior wall of the lens capsule), vitreous, vitreous chamber, retina, optic nerve (i.e. the optic disc), and blood vessels and nerves which vascularize or innervate a posterior ocular region or site.

Thus, a posterior ocular condition can include a disease, ailment or condition, such as for example, acute macular neuroretinopathy; Behcet's disease; choroidal neovascularization; diabetic uveitis; histoplasmosis; infections, such as fungal or viral-caused infections; macular degeneration, such as acute macular degeneration, non-exudative age related macular degeneration and exudative age related macular degeneration; edema, such as macular edema, cystoid macular edema and diabetic macular edema; multifocal choroiditis; ocular trauma which affects a posterior ocular site or location; ocular tumors; retinal disorders, such as central retinal vein occlusion, diabetic retinopathy (including proliferative diabetic retinopathy), proliferative vitreoretinopathy (PVR), retinal arterial occlusive disease, retinal detachment, uveitic retinal disease; sympathetic ophthalmia; Vogt Koyanagi-Harada (VKH) syndrome; uveal diffusion; a posterior ocular condition caused by or influenced by an ocular laser treatment; posterior ocular conditions caused by or influenced by a photodynamic therapy, photocoagulation, radiation retinopathy, epiretinal membrane disorders, branch retinal vein occlusion, anterior ischemic optic neuropathy, non-retinopathy diabetic retinal dysfunction, retinitis pigmentosa, and glaucoma. Glaucoma can be considered a posterior ocular condition because the therapeutic goal is to prevent the loss of or reduce the occurrence of loss of vision due to damage to or loss of retinal cells or optic nerve cells (i.e. neuroprotection).

"Biodegradable polymer" means a polymer or polymers which degrade in vivo, and wherein erosion of the polymer or polymers over time occurs concurrent with or subsequent to release of the therapeutic agent. Specifically, hydrogels such as methylcellulose which act to release drug through polymer swelling are specifically excluded from the term "biodegradable polymer". The terms "biodegradable" and "bioerodible" are equivalent and are used interchangeably herein. A biodegradable polymer may be a homopolymer, a copolymer, or a polymer comprising more than two different polymeric units.

"Treat", "treating", or "treatment" means a reduction or resolution or prevention of an ocular condition, ocular injury or damage, or to promote healing of injured or damaged ocular tissue.

"Therapeutically effective amount" means the level or amount of agent needed to treat an ocular condition, or reduce or prevent ocular injury or damage without causing significant negative or adverse side effects to the eye or a region of the eye.

Intraocular implants in accordance with the disclosure herein comprise a therapeutic component and a drug release sustaining component associated with the therapeutic component. In accordance with the present invention, the therapeutic component comprises, consists essentially of, or consists of, an alpha-2 adrenergic receptor agonist. The alpha-2 adrenergic receptor agonist may be an agonist or agent that selectively activates alpha-2 adrenergic receptors, for example by binding to an alpha-2 adrenergic receptor, relative to other types of adrenergic receptors, such as alpha-1 adrenergic receptors. The selective activation can be achieved under different conditions, but preferably, the selective activation is determined under physiological conditions, such as conditions associated with an eye of a human or animal patient. The drug release sustaining component is associated with the therapeutic component to sustain release of an amount of the alpha-2 adrenergic receptor agonist into an eye in which the implant is placed. The amount of the alpha-2 adrenergic receptor agonist is released into the eye for a period of time greater than about one week after the implant is placed in the eye and is effective in preventing, reducing or treating an ocular disease or condition such as glaucoma, neurodegeneration, a retinal disorder or condition or an ocular vasculopathy, such as vascular occlusion.

In one embodiment, the intraocular implants comprise an alpha-2 adrenergic receptor agonist and a biodegradable polymer matrix. The alpha-2 adrenergic receptor agonist is associated with a biodegradable polymer matrix that degrades at a rate effective to sustain release of an amount of the agonist from the implant for a time sufficient to reduce or prevent an ocular vascular occlusion. The intraocular implant is biodegradable or bioerodible and provides a sustained release of the alpha-2 adrenergic receptor agonist in an eye for extended periods of time, such as for more than one week, for example for about three months or more and up to about six months or more. In certain implants, the alpha-2 adrenergic receptor agonist is released for about 30-35 days or less. In other implants, the alpha-2 adrenergic receptor agonist is released for 40 days or more.

The biodegradable polymer component of the foregoing implants may be a mixture of biodegradable polymers, wherein at least one of the biodegradable polymers is a polylactic acid polymer having a molecular weight less than 64 kiloDaltons (kD). Additionally or alternatively, the foregoing implants may comprise a first biodegradable polymer of a polylactic acid, and a different second biodegradable polymer of a polylactic acid. Furthermore, the foregoing implants may comprise a mixture of different biodegradable polymers, each biodegradable polymer having an inherent viscosity in a range from about 0.2 (or about 0.3) deciliters/gram (dl/g) to about 1.0 dl/g.

The alpha-2 adrenergic receptor agonist of the implants disclosed herein may include quinoxaline derivatives, or other agonists that are effective in treating ocular conditions. One example of a suitable quinoxaline derivative is brimonidine or brimonidine tartrate. In addition, the therapeutic component of the present implants may include one or more additional and different therapeutic agents that may be effective in treating an ocular condition.

A method of making the present implants involves combining or mixing the alpha-2 adrenergic receptor agonist with a biodegradable polymer or polymers. The mixture may then be extruded or compressed to form a single composition. The single composition may then be processed to form individual implants suitable for placement in an eye of a patient.

The implants may be placed in an ocular region to treat a variety of ocular conditions, including conditions such as ocular vasculopathies that affect an anterior region or posterior region of an eye. For example, the implants may be used to treat many conditions of the eye, including, without limitation, conditions associated with vascular occlusion.

Kits in accordance with the present invention may comprise one or more of the present implants, and instructions for using the implants. For example, the instructions may explain how to administer the implants to a patient, and types of conditions that may be treated with the implants.

The present invention also encompasses a biodegradable intraocular implant for improving vision. The implant can comprise an alpha-2 adrenergic receptor agonist and a biodegradable polymer. The implant releases the alpha-2 adrenergic receptor agonist from the polymer, upon intravitreal placement of the implant, in an amount effective to improve the vision of the eye in which the implant is placed. The alpha-2 adrenergic receptor agonist can be a quinoxaline, such as a (2-imidazolin-2-ylamino)quinoxaline, a 5-bromo-6-(2-imidazolin-2-ylamino)quinoxaline, and derivatives thereof and mixtures thereof. Thus, the alpha-2 adrenergic receptor agonist can be a brimonidine or salts thereof or mixtures thereof. For example, the alpha-2 adrenergic receptor agonist can be brimonidine tartrate.

The alpha-2 adrenergic receptor agonist can be dispersed within the biodegradable polymer of the implant. The biodegradable polymer can comprise a mixture of a first biodegradable polymer of polylactic acid, and a different second biodegradable polymer of polylactic acid. The polymer can release drug at a rate effective to sustain release of an amount of the alpha-2 adrenergic receptor agonist from the implant for more than one month or for more that forty days or for less than thirty five days from the time the implant is placed in the vitreous of the eye.

An embodiment of the present invention is a method of making a biodegradable intraocular implant by extruding a mixture of an alpha-2 adrenergic receptor agonist and a biodegradable polymer component to form a biodegradable material that releases drug at a rate effective to sustain release of an amount of the alpha-2 adrenergic receptor agonist from the implant for a time effective to improve vision in an eye in which the implant is placed.

A further embodiment of the present invention is a method for improving or for maintaining vision by placing in the vitreous of an eye a biodegradable intraocular implant comprising an alpha-2 adrenergic receptor agonist associated with a biodegradable polymer, thereby improving or maintaining vision. This method can be used to treat an ocular condition such as: macular degeneration, macular edema, retinal arterial occlusive disease, central retinal vein occlusion, disseminated intravascular coagulopathy, branch retinal vein occlusion, hypertensive fundus changes, ocular ischemic syndrome, retinal arterial microaneurysms, hemi-retinal vein occlusion, central retinal artery occlusion, branch retinal artery occlusion, carotid artery disease (cad), eales disease, vasculopathies associated with diabetes, Non-Exudative Age Related Macular Degeneration, Exudative Age Related Macular Degeneration, Choroidal Neovascularization, Diabetic Retinopathy, Acute Macular Neuroretinopathy, Central Serous Chorioretinopathy, Cystoid Macular Edema, Diabetic Macular Edema, Acute Multifocal Placoid Pigment Epitheliopathy, Behcet's Disease, Birdshot Retinochoroidopathy, Syphilis, Lyme, Tuberculosis, Toxoplasmosis, Intermediate Uveitis, Multifocal Choroiditis, Multiple Evanescent White Dot Syndrome, Ocular Sarcoidosis, Posterior Scleritis, Serpiginous Choroiditis, Subretinal Fibrosis and Uveitis Syndrome, Vogt-Koyanagi-Harada Syndrome, Coat's Disease, Parafoveal Telangiectasia, Papillophlebitis, Frosted Branch Angiitis, Sickle Cell Retinopathy and other Hemoglobinopathies, Angioid Streaks, Familial Exudative Vitreoretinopathy, Sympathetic Ophthalmia, Uveitic Retinal Disease, Retinal Detachment, Trauma, Laser, photodynamic therapy, Photocoagulation, Hypoperfusion During Surgery, Radiation Retinopathy, Bone Marrow Transplant Retinopathy, Proliferative Vitreal Retinopathy and Epiretinal Membranes, Proliferative Diabetic Retinopathy, Ocular Histoplasmosis, Ocular Toxocariasis, Presumed Ocular Histoplasmosis Syndrome, Endophthalmitis, Toxoplasmosis, Retinal Diseases Associated with HIV Infection, Choroidal Disease Associated with HIV Infection, Uveitic Disease Associated with HIV Infection, Viral Retinitis, Acute Retinal Necrosis, Progressive Outer Retinal Necrosis, Fungal Retinal Diseases, Ocular Syphilis, Ocular Tuberculosis, Diffuse Unilateral Subacute Neuroretinitis, Myiasis, Retinitis Pigmentosa, Systemic Disorders with Associated Retinal Dystrophies, Congenital Stationary Night Blindness, Cone Dystrophies, Stargardt's Disease and Fundus Flavimaculatus, Best's Disease, Pattern Dystrophy of the Retinal Pigmented Epithelium, X-Linked Retinoschisis, Sorsby's Fundus Dystrophy, Benign Concentric Maculopathy, Bietti's Crystalline Dystrophy, pseudoxanthoma elasticum, Retinal Detachment, Macular Hole, Giant Retinal Tear, Retinal Disease Associated with Tumors, Congenital Hypertrophy of the RPE, Posterior Uveal Melanoma, Choroidal Hemangioma, Choroidal Osteoma, Choroidal Metastasis, Combined Hamartoma of the Retina and Retinal Pigmented Epithelium, Retinoblastoma, Vasoproliferative Tumors of the Ocular Fundus, Retinal Astrocytoma, Intraocular Lymphoid Tumors, Punctate Inner Choroidopathy, Acute Posterior Multifocal Placoid Pigment Epitheliopathy, Myopic Retinal Degeneration, and Acute Retinal Pigment Epithelitis.

The implant can release the alpha-2 adrenergic receptor agonist from the polymer, upon intravitreal placement of the implant, for a period of about ninety days. Significantly, the alpha-2 adrenergic receptor agonist can be retained in the retina for a period of time longer than it is retained in the vitreous. An embodiment of the present invention is a method for improving, maintaining, restoring or repairing vision, the method comprising the step of placing in the vitreous of an eye a biodegradable intraocular implant comprising a brimonidine associated with a biodegradable polymer, thereby improving, maintaining, restoring or repairing vision.

An embodiment of our invention is a biodegradable intraocular implant comprising an alpha-2 adrenergic receptor agonist and a biodegradable polymer, wherein the biodegradable polymer comprises an ester end-capped biodegradable polymer and an acid end-capped biodegradable polymer. The implant can comprise from about 10% to about 91% ester end-capped biodegradable polymer, from about 5 wt % to about 40 wt % acid end-capped biodegradable polymer, and from about 4 wt % to about 50 wt % alpha-2 adrenergic receptor agonist. Preferably, the implant can comprise from about 45% to about 80% ester end-capped biodegradable polymer, from about 10 wt % to about 40 wt % acid end-capped biodegradable polymer, and about 10 wt % to about 15 wt % alpha-2 adrenergic receptor agonist. More preferably, the implant can comprise about 88 wt % ester end-capped biodegradable polymer, about 10 wt % acid end-capped biodegradable polymer, and about 12 wt % alpha-2 adrenergic receptor agonist. Most preferably, the implant can comprise from about 53 wt % to about 73% ester end-capped biodegradable polymer, from about 15 wt % to about 35 wt % acid end-capped biodegradable polymer, and from about 9 wt % to about 12 wt % alpha-2 adrenergic receptor agonist.

The biodegradable polymer of the implant can comprise more than one ester end-capped biodegradable polymer. Alternately, the biodegradable polymer of the implant can comprise more than one acid end-capped biodegradable polymer. The implant can have no or a nominal lag time after ocular implantation or insertion of the implant before release of a therapeutically effective amount of the alpha-2 adrenergic receptor agonist from the implant occurs. The implant comprise greater than or equal to 4 weight percent (wt %) of a biologically active alpha-2 adrenergic receptor agonist and the implant preferably does not include any pore forming additives, release rate modulators or release rate modifiers. The implant can exhibit a sustained release of the alpha-2 adrenergic receptor agonist from the biodegradable polymeric matrix over a period of at least 115 days. Additionally, the implant can exhibit a substantially linear release of the alpha-2 adrenergic receptor agonist from the biodegradable polymeric matrix of the implant over a period of time from about 20 days to about 50 days.

A preferred embodiment of a biodegradable intraocular implant within the scope of our invention can comprise an alpha-2 adrenergic receptor agonist, and a biodegradable polymer, wherein the biodegradable polymer comprises an ester end-capped biodegradable polymer and an acid end-capped biodegradable polymer, wherein the implant comprises from about 40% to about 91% of at least two different ester end-capped biodegradable polymers, from about 5 wt % to about 40 wt % acid end-capped biodegradable polymer, and from about 4 wt % to about 20 wt % alpha-2 adrenergic receptor agonist.

Our invention also includes a process for making a biodegradable intraocular implant by mixing an alpha-2 adrenergic receptor agonist and a biodegradable polymer, wherein the biodegradable polymer comprises an ester end-capped biodegradable polymer and an acid end-capped biodegradable polymer; heating the mixture, and; extruding the heated mixture, to thereby make a biodegradable intraocular implant.

An implant within the scope of our invention can be an extruded filament with a diameter of about 0.5 mm, a length of about 6 mm and a weight of about 1 mg. The alpha-2 adrenergic receptor agonist can be homogenously distributed throughout the implant.

Our implants can be used to treat ocular conditions by intraocular administration of a biodegradable intraocular implant comprising an alpha-2 adrenergic receptor agonist and a biodegradable polymer, wherein the biodegradable polymer comprises an ester end-capped biodegradable polymer and an acid end-capped biodegradable polymer. The alpha-2 adrenergic receptor agonist can be selected from the group consisting of brimonidine, salts thereof, and mixtures thereof.

In another embodiment of our invention a biodegradable intraocular implant can comprise a plurality of forms of an alpha-2 adrenergic receptor agonist and a biodegradable polymer. The alpha-2 adrenergic receptor agonist can be a brimonidine and the brimonidine can be present in two forms in the implant. The two forms of brimonidine present in the implant can be brimonidine free base and brimonidine tartrate. Such and implant can comprises from about 50 wt % to about 70% ester end-capped biodegradable polymer, from about 1 wt % to about 49 wt % brimonidine free base and from about 1 wt % to about 49 wt % brimonidine tartrate. Alternately, the implant can comprises from about 50 wt % to about 60% ester end-capped biodegradable polymer, from about 1 wt % to about 49 wt % brimonidine free base and from about 1 wt % to about 49 wt % brimonidine tartrate. More preferably, the implant can comprise from about 50 wt % to about 70% ester end-capped biodegradable polymer, from about 10 wt % to about 30 wt % brimonidine free base and from about 10 wt % to about 30 wt % brimonidine tartrate. In most preferred embodiment the implant can comprise from about 55 wt % to about 65% ester end-capped biodegradable polymer, from about 15 wt % to about 20 wt % brimonidine free base and from about 15 wt % to about 20 wt % brimonidine tartrate, for example the implant can comprise about 65 wt % ester end-capped biodegradable polymer, about 18 wt % brimonidine free base and about 18 wt % brimonidine tartrate. The implant of claim 21, wherein the biodegradable polymer comprises more than one ester end-capped biodegradable polymer. And the implant can have no burst release and no or a nominal lag time after ocular implantation or insertion of the implant before release of a therapeutically effective amount of the alpha-2 adrenergic receptor agonist from the implant occurs. Additionally, the implant can exhibit a sustained release of the alpha-2 adrenergic receptor agonist from the biodegradable polymeric matrix over a period of at least 60 days.

Furthermore, the implant can exhibits a substantially linear release of the alpha-2 adrenergic receptor agonist from the biodegradable polymeric matrix of the implant over a period of time from about 20 days to about 50 days.

A preferred embodiment of our invention can comprise a brimonidine free base; a brimonidine tartrate, and an ester end-capped biodegradable polymer, wherein the implant comprises from about 50 wt % to about 70% of the ester end-capped biodegradable polymer, from about 1 wt % to about 49 wt % of the brimonidine free base and from about 1 wt % to about 49 wt % of the brimonidine tartrate.

Our invention encompasses a process for making a biodegradable intraocular implant comprising (a) mixing a plurality of forms of alpha-2 adrenergic receptor agonist and a biodegradable polymer; (b) heating the mixture, and; (c) extruding the heated mixture, to thereby make a biodegradable intraocular implant. The implant can be extruded as a filament with a diameter of about 0.5 mm, a length of about 6 mm and a weight of about 1 mg. The implant can also be made by a direct compression or solvent extraction method. The shape of the implant can also be as a tablet, pellet or rod.

Finally, our invention encompasses a method of treating a symptom of glaucoma by placing a biodegradable intraocular implant comprising an alpha-2 adrenergic receptor agonist associated with a biodegradable polymer into the vitreous of an eye, thereby treating a symptom of the glaucoma. The symptom of the glaucoma can be reduced for at least about 35 days after intravitreal placement of the implant. The symptom of the glaucoma treated can be an elevated intraocular pressure.

Additional aspects and advantages of the present invention are set forth in the following description and claims, particularly when considered in conjunction with the accompanying drawings.

DRAWINGS

FIG. 1 is a graph showing in vitro cumulative total release of brimonidine free base ("BFB") (y axis) over time in days (X axis) from three different polymeric implants made according to the method of Example 1. The legend in Figure gives for each of the three implants the seven digit, hyphenated formulation number followed by the weight percent of BFB in the implant (i.e. "35-API" means 35 wt % BFB), and then the weight percents of each of the three polymers used to make each of the three implants shown.

FIG. 2 is a graph showing in vitro cumulative total release of two BFB plus BT polymeric implant formulations compared to a BFB only polymeric implant, the axes and legend being formatted as in FIG. 1.

FIG. 4 is a graph showing in vitro cumulative total release from three BFB bar shaped implants, as set forth in Example 3.

FIG. 5 is a graph showing in vitro cumulative total release from a BFB disc shaped implant, as set forth in Example 3.

FIG. 6 is a graph showing change of IOP over a 63 day period from baseline IOP at day zero in rabbits that had received sub-tenon administration of six 400 ug BT bars (2400 μg brimonidine tartrate), as set forth in Example 3.

DESCRIPTION

Figure 3A:
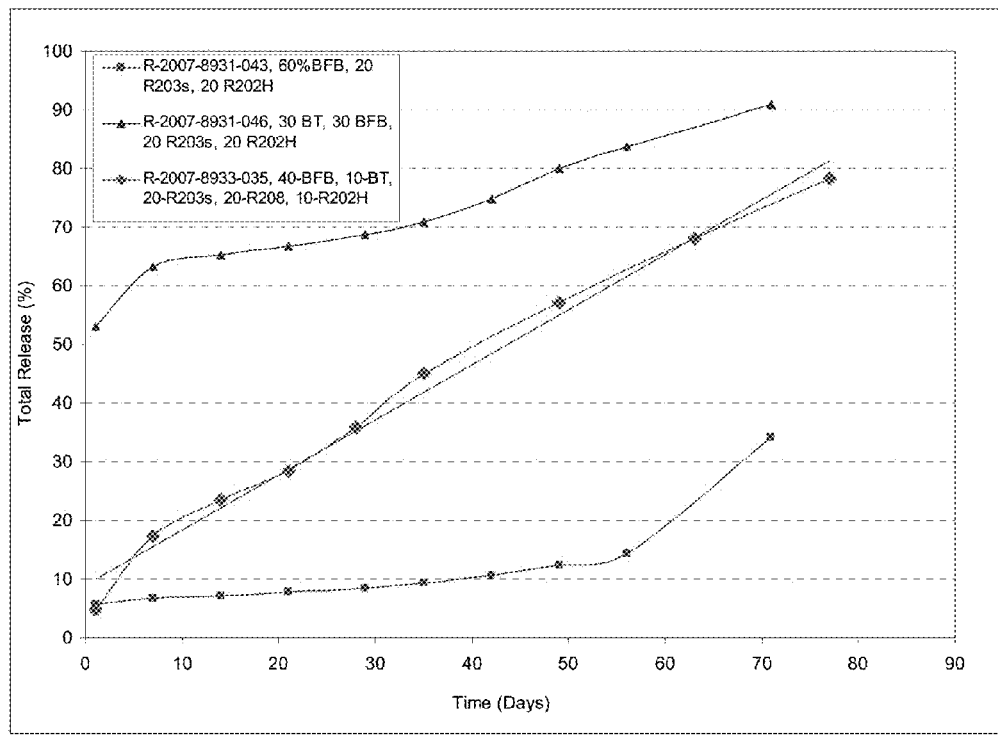
FIG. 3a is a drawing of a bar shaped implant and FIG. 3b is a drawing of a disc shaped implant, showing exemplary implant dimensions, as explained in Example 3.
Figure 3B:
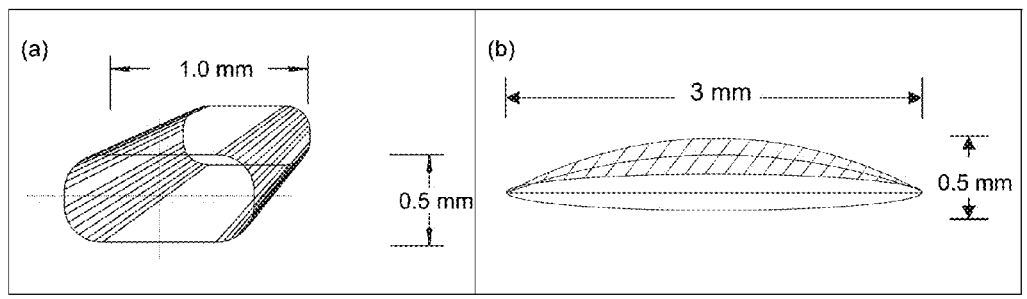

Our invention is based on the discovery of novel formulations and configurations of one or more forms of an alpha-2-selective adrenergic receptor agonist therapeutic agent and a biodegradable polymer which once heat extruded, or made by injection molding, form implants suitable for intraocular administration to treat ocular diseases and conditions. Embodiments of our invention have substantially linear therapeutic agent release characteristics and/or high l (greater than 50 wt %) drug load in the implant.

The implants comprise a pharmaceutically acceptable polymeric composition and are formulated to release one or more pharmaceutically active agents, such as alpha-2 adrenergic receptor agonists, over an extended period of time. The implants are effective to provide a therapeutically effective dosage of the agent or agents directly to a region of the eye to treat or prevent one or more undesirable ocular conditions. Thus, with a single administration, therapeutic agents will be made available at the site where they are needed and will be maintained for an extended period of time, rather than subjecting the patient to repeated injections or, in the case of self-administered drops, ineffective treatment with only limited bursts of exposure to the active agent or agents.

An intraocular implant in accordance with the disclosure herein comprises a therapeutic component and a drug release sustaining component associated with the therapeutic component. In accordance with the present invention, the therapeutic component comprises, consists essentially of, or consists of, an alpha-2 adrenergic receptor agonist. The drug release sustaining component is associated with the therapeutic component to sustain release of a therapeutically effective amount of the alpha-2 adrenergic receptor agonist into an eye in which the implant is placed. The therapeutic amount of the alpha-2 adrenergic receptor agonist is released into the eye for a period of time greater than about one week after the implant is placed in the eye.

Intraocular implants have been developed which can release drug loads over various' time periods. These implants, which when inserted into an eye, such as the vitreous of an eye, provide therapeutic levels of an alpha-2 adrenergic receptor agonist for extended periods of time (e.g., for about 1 week or more). The implants disclosed are effective in treating ocular conditions, such as posterior ocular conditions.

In one embodiment of the present invention, an intraocular implant comprises a biodegradable polymer matrix. The biodegradable polymer matrix is one type of a drug release sustaining component. The biodegradable polymer matrix is effective in forming a biodegradable intraocular implant. The biodegradable intraocular implant comprises an alpha-2 adrenergic receptor agonist associated with the biodegradable polymer matrix. The matrix degrades at a rate effective to sustain release of an amount of the alpha-2 adrenergic receptor agonist for a time greater than about one week from the time in which the implant is placed in ocular region or ocular site, such as the vitreous of an eye.

The alpha-2 adrenergic receptor agonist of the implant is typically an agent that selectively activates alpha-2 adrenergic receptors relative to alpha-1 adrenergic receptors. In certain implants, the alpha-2 adrenergic receptor agonist selectively activates a subtype of the alpha-2 adrenergic receptors. For example, the agonist may selectively activate one or more of the alpha-2a, the alpha-2b, or the alpha-2c receptors, under certain conditions, such as physiological conditions. Under other conditions, the agonist of the implant may not be selective for alpha-2 adrenergic receptor subtypes. The agonist may activate the receptors by binding to the receptors, or by any other mechanism.

In certain implants, the alpha-2 adrenergic receptor agonist is a quinoxaline derivative. The quinoxaline derivatives useful in the present implants are those quinoxaline derivatives having the formula,

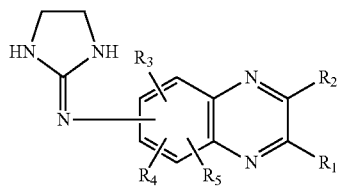

pharmaceutically acceptable acid addition salts thereof, and mixtures thereof. $R_1$ and $R_2$ each is independently selected from the group consisting of H, alkyl radicals containing 1 to 4 carbon atoms and alkoxy radicals containing 1 to 4 carbon atoms. $R_2$ is preferably a methyl radical. The 2-imidazolin-2-ylamino group may be in any of the 5-, 6-, 7- and 8-positions, preferably in the 6-position, of the quinoxaline nucleus. $R_3$, $R_4$ and $R_5$ each is located in one of the remaining 5-, 6-, 7- or 8-positions of the quinoxaline nucleus and is independently selected from the group consisting of Cl, Br, H and alkyl radicals containing 1 to 3 carbon atoms. $R_3$ is preferably in the 5-position of the quinoxaline nucleus, and $R_4$ and $R_5$ are preferably both H. In a particularly useful embodiment $R_3$ is Br.

In at least one implant, $R_1$ is H and $R_2$ is selected from alkyl radicals containing 1 to 4 carbon atoms. $R_3$ may advantageously be in the 5-position of the quinoxaline nucleus and be selected from H and alkyl radicals containing 1 to 3 carbon atoms. All stereoisomers, tautomers and mixtures thereof which comply with the constraints of one or more of the presently useful compounds are included within the scope of the present invention.

Pharmaceutically acceptable acid addition salts of the compounds of the invention are those formed from acids which form non-toxic addition salts containing pharmaceutically acceptable anions, such as the hydrochloride, hydrobromide, hydroiodide, sulfate, or bisulfate, phosphate or acid phosphate, acetate, maleate, fumarate, oxalate, lactate, tartrate, citrate, gluconate, saccharate and p-toluene sulphonate salts.

In more specific implants, the quinoxaline derivative has the formula

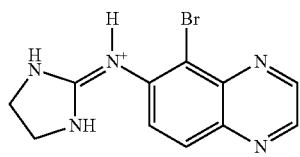 [SMILES: Brc1c([NH+]=C2NCCN2)ccc2nccnc12]

In additional implants, the alpha-2 adrenergic receptor agonist is provided as a salt having the formula

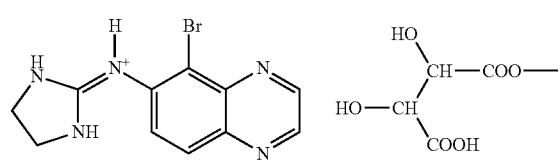

The foregoing salt is known as brimonidine tartrate (AGN 190342-F, 5-bromo-6-(2-imidazolidinylideneamino)quinoxaline tartrate), and is publicly available from Allergan, Inc. under the tradename Alphagan-P®. Brimonidine, an organic base, is publicly available as either brimonidine tartrate salt or as brimonidine freebase. The tartrate salt is more soluble than the freebase in various aqueous media. Since both the tartrate salt and the freebase are chemically stable and have melting points higher than 200° C., both forms are suitable in forming the present implants.

Thus, the implant may comprise a therapeutic component which comprises, consists essentially of, or consists of a brimonidine salt, such as brimonidine tartrate, a brimonidine free base, or mixtures thereof.

The alpha-2 adrenergic receptor agonist may be in a particulate or powder form and entrapped by the biodegradable polymer matrix. Usually, alpha-2 adrenergic receptor agonist particles will have an effective average size less than about 3000 nanometers. In certain implants, the particles may have an effective average particle size about an order of magnitude smaller than 3000 nanometers. For example, the particles may have an effective average particle size of less than about 500 nanometers. In additional implants, the particles may have an effective average particle size of less than about 400 nanometers, and in still further embodiments, a size less than about 200 nanometers.

The alpha-2 adrenergic receptor agonist of the implant is preferably from about 10% to 90% by weight of the implant. More preferably, the alpha-2 adrenergic receptor agonist is from about 20% to about 80% by weight of the implant. In a preferred embodiment, the alpha-2 adrenergic receptor agonist comprises about 20% by weight of the implant (e.g., 15%-25%). In another embodiment, the alpha-2 adrenergic receptor agonist comprises about 50% by weight of the implant.

Suitable polymeric materials or compositions for use in the implant include those materials which are compatible, that is biocompatible, with the eye so as to cause no substantial interference with the functioning or physiology of the eye. Such materials preferably are at least partially and more preferably substantially completely biodegradable or bioerodible.

Examples of useful polymeric materials include, without limitation, such materials derived from and/or including organic esters and organic ethers, which when degraded result in physiologically acceptable degradation products, including the monomers. Also, polymeric materials derived from and/or including, anhydrides, amides, orthoesters and the like, by themselves or in combination with other monomers, may also find use. The polymeric materials may be addition or condensation polymers, advantageously condensation polymers. The polymeric materials may be cross-linked or non-cross-linked, for example not more than lightly cross-linked, such as less than about 5%, or less than about 1% of the polymeric material being cross-linked. For the most part, besides carbon and hydrogen, the polymers will include at least one of oxygen and nitrogen, advantageously oxygen. The oxygen may be present as oxy, e.g. hydroxy or ether, carbonyl, e.g. non-oxo-carbonyl, such as carboxylic acid ester, and the like. The nitrogen may be present as amide, cyano and amino. The polymers set forth in Heller, Biodegradable Polymers in Controlled Drug Delivery, In: CRC Critical Reviews in Therapeutic Drug Carrier Systems, Vol. 1, CRC Press, Boca Raton, Fla. 1987, pp 39-90, which describes encapsulation for controlled drug delivery, may find use in the present implants.

Of additional interest are polymers of hydroxyaliphatic carboxylic acids, either homopolymers or copolymers, and polysaccharides. Polyesters of interest include polymers of D-lactic acid, L-lactic acid, racemic lactic acid, glycolic acid, polycaprolactone, and combinations thereof. Generally, by employing the L-lactate or D-lactate, a slowly eroding polymer or polymeric material is achieved, while erosion is substantially enhanced with the lactate racemate.

Among the useful polysaccharides are, without limitation, calcium alginate, and functionalized celluloses, particularly carboxymethylcellulose esters characterized by being water insoluble, a molecular weight of about 5 kD to 500 kD, for example.

Other polymers of interest include, without limitation, polyvinyl alcohol, polyesters, polyethers and combinations thereof which are biocompatible and may be biodegradable and/or bioerodible.

Some preferred characteristics of the polymers or polymeric materials for use in the present invention may include biocompatibility, compatibility with the therapeutic component, ease of use of the polymer in making the drug delivery systems of the present invention, a half-life in the physiological environment of at least about 6 hours, preferably greater than about one day, not significantly increasing the viscosity of the vitreous, and water insolubility.

The biodegradable polymeric materials which are included to form the matrix are desirably subject to enzymatic or hydrolytic instability. Water soluble polymers may be cross-linked with hydrolytic or biodegradable unstable cross-links to provide useful water insoluble polymers. The degree of stability can be varied widely, depending upon the choice of monomer, whether a homopolymer or copolymer is employed, employing mixtures of polymers, and whether the polymer includes terminal acid groups.

Equally important to controlling the biodegradation of the polymer and hence the extended release profile of the implant is the relative average molecular weight of the polymeric composition employed in the implant. Different molecular weights of the same or different polymeric compositions may be included in the implant to modulate the release profile. In certain implants, the relative average molecular weight of the polymer will range from about 9 to about 64 kD, usually from about 10 to about 54 kD, and more usually from about 12 to about 45 kD.

In some implants, copolymers of glycolic acid and lactic acid are used, where the rate of biodegradation is controlled by the ratio of glycolic acid to lactic acid. The most rapidly degraded copolymer has roughly equal amounts of glycolic acid and lactic acid. Homopolymers, or copolymers having ratios other than equal, are more resistant to degradation. The ratio of glycolic acid to lactic acid will also affect the brittleness of the implant, where a more flexible implant is desirable for larger geometries. The % of polylactic acid in the polylactic acid polyglycolic acid (PLGA) copolymer can be 0-100%, preferably about 15-85%, more preferably about 35-65%. In some implants, a 50/50 PLGA copolymer is used.

The biodegradable polymer matrix of the intraocular implant may comprise a mixture of two or more biodegradable polymers. For example, the implant may comprise a mixture of a first biodegradable polymer and a different second biodegradable polymer. One or more of the biodegradable polymers may have terminal acid groups.

Release of a drug from an erodible polymer is the consequence of several mechanisms or combinations of mechanisms. Some of these mechanisms include desorption from the implants surface, dissolution, diffusion through porous channels of the hydrated polymer and erosion. Erosion can be bulk or surface or combination of both. As discussed herein, the matrix of the intraocular implant may release drug at a rate effective to sustain release of an amount of the alpha-2 adrenergic receptor agonist for more than one week after implantation into an eye. In certain implants, therapeutic amounts of the alpha-2 adrenergic receptor agonist are released for no more than about 30-35 days after implantation. For example, an implant may comprise brimonidine tartrate, and the matrix of the implant degrades at a rate effective to sustain release of a therapeutically effective amount of brimonidine tartrate for about one month after being placed in an eye. As another example, the implant may comprise brimonidine tartrate, and the matrix releases drug at a rate effective to sustain release of a therapeutically effective amount of brimonidine tartrate for more than forty days, such as for about six months.

One example of the biodegradable intraocular implant comprises an alpha-2 adrenergic receptor agonist associated with a biodegradable polymer matrix, which comprises a mixture of different biodegradable polymers. At least one of the biodegradable polymers can be polylactide having a molecular weight of from about 40 to about 80 kD. A second biodegradable polymer can be a polylactide having a molecular weight from about 10 to 20 kD. Such a mixture is effective in sustaining release of a therapeutically effective amount of the alpha-2 adrenergic receptor agonist for a time period greater than about one month from the time the implant is placed in an eye.

Another example of a biodegradable intraocular implant comprises an alpha-2 adrenergic receptor agonist associated with a biodegradable polymer matrix, which comprises a mixture of different biodegradable polymers, each biodegradable polymer having an inherent viscosity from about 0.16 dl/g to about 1.0 dl/g. For example, one of the biodegradable polymers may have an inherent viscosity of about 0.3 dl/g. A second biodegradable polymer may have an inherent viscosity of about 1.0 dl/g. The inherent viscosities identified above may be determined in 0.1% chloroform at 25° C.

One particular implant comprises brimonidine tartrate associated with a combination of two different polylactide polymers. The brimonidine tartrate can present at up to about 60% by weight of the implant. One polylactide polymer can have a molecular weight of about 14 kD and an inherent viscosity of about 0.3 dl/g, and the other polylactide polymer can have a molecular weight of about 63.3 kD and an inherent viscosity of about 1.0 dl/g. The two polylactide polymers can be present in the implant in a 1:1 ratio. Such an implant provides for release of the brimonidine for more than two months in vitro, as described herein. The implant is provided in the form of a rod, bar or disc or a filament produced by an extrusion or injection molding process.

The release of the alpha-2 adrenergic receptor agonist from the intraocular implant comprising a biodegradable polymer matrix may include an initial burst of release followed by a gradual increase in the amount of the alpha-2 adrenergic receptor agonist released, or the release may include an initial delay in release of the alpha-2 adrenergic receptor agonist followed by an increase in release. When the implant is substantially completely degraded, the percent of the alpha-2 adrenergic receptor agonist that has been released is about one hundred. Compared to existing implants, the implants disclosed herein do not completely release, or release about 100% of the alpha-2 adrenergic receptor agonist, until after about one week of being placed in an eye.

It may be desirable to provide a relatively constant rate of release of the alpha-2 adrenergic receptor agonist from the implant over the life of the implant. For example, it may be desirable for the alpha-2 adrenergic receptor agonist to be released in amounts from about 0.01 µg to about 2 µg per day for the life of the implant. However, the release rate may change to either increase or decrease depending on the formulation of the biodegradable polymer matrix. In addition, the release profile of the alpha-2 adrenergic receptor agonist may include one or more linear portions and/or one or more non-linear portions. Preferably, the release rate is greater than zero once the implant has begun to degrade or erode.

The implants may be monolithic, i.e. having the active agent or agents homogenously distributed through the polymeric matrix, or encapsulated, where a reservoir of active agent is encapsulated by the polymeric matrix or as a core-shell type of implant. Due to ease of manufacture, monolithic implants are usually preferred over encapsulated forms. However, the greater control afforded by the encapsulated, reservoir-type implant may be of benefit in some circumstances, where the therapeutic level of the drug falls within a narrow window. In addition, the therapeutic component, including the alpha-2 adrenergic receptor agonist, may be distributed in a non-homogenous pattern in the matrix. For example, the implant may include a portion that has a greater concentration of the alpha-2 adrenergic receptor agonist relative to a second portion of the implant.

The intraocular implants disclosed herein may have a size of between about 5 µm and about 2 mm, or between about 10 µm and about 1 mm for administration with a needle, greater than 1 mm, or greater than 2 mm, such as 3 mm or up to 10 mm, for administration by surgical implantation. The vitreous chamber in humans is able to accommodate relatively large implants of varying geometries, having lengths of, for example, 1 to 10 mm. The implant may be a cylindrical pellet (e.g., rod) with dimensions of about 2 mm×0.75 mm diameter. Or the implant may be a cylindrical pellet with a length of about 7 mm to about 10 mm, and a diameter of about 0.75 mm to about 1.5 mm.

The implants may also be at least somewhat flexible so as to facilitate both insertion of the implant in the eye, such as in the vitreous, and accommodation of the implant. The total weight of the implant is usually about 250-5000 µg, more preferably about 500-1000 µg. For example, an implant may be about 500 µg, or about 1000 µg. For non-human individuals, the dimensions and total weight of the implant(s) may be larger or smaller, depending on the type of individual. For example, humans have a vitreous volume of approximately 3.8 ml, compared with approximately 30 ml for horses, and approximately 60-100 ml for elephants. An implant sized for use in a human may be scaled up or down accordingly for other animals, for example, about 8 times larger for an implant for a horse, or about, for example, 26 times larger for an implant for an elephant.

Thus, implants can be prepared where the center may be of one material and the surface may have one or more layers of the same or a different composition, where the layers may be cross-linked, or of a different molecular weight, different density or porosity, or the like. For example, where it is desirable to quickly release an initial bolus of drug, the center may be a polylactate coated with a polylactate-polyglycolate copolymer, so as to enhance the rate of initial degradation. Alternatively, the center may be polyvinyl alcohol coated with polylactate, so that upon degradation of the polylactate exterior the center would dissolve and be rapidly washed out of the eye.

The implants may be of any geometry including fibers, sheets, films, microspheres, spheres, circular discs, plaques and the like. The upper limit for the implant size will be determined by factors such as toleration for the implant, size limitations on insertion, ease of handling, etc. Where sheets or films are employed, the sheets or films will be in the range of at least about 0.5 mm×0.5 mm, usually about 3-10 mm×5-10 mm with a thickness of about 0.1-1.0 mm for ease of handling. Where fibers are employed, the fiber diameter will generally be in the range of about 0.05 to 3 mm and the fiber length will generally be in the range of about 0.5-10 mm. Spheres may be in the range of 0.5 µm to 4 mm in diameter, with comparable volumes for other shaped particles.

The size and form of the implant can also be used to control the rate of release, period of treatment, and drug concentration at the site of implantation. Larger implants will deliver a proportionately larger dose, but depending on the surface to mass ratio, may have a slower release rate. The particular size and geometry of the implant are chosen to suit the site of implantation.

The proportions of alpha-2 adrenergic receptor agonist, polymer, and any other modifiers may be empirically determined by formulating several implants with varying proportions. A USP approved method for dissolution or release test can be used to measure the rate of release (USP 23; NF 18 (1995) pp. 1790-1798). For example, using the infinite sink method, a weighed sample of the implant is added to a measured volume of a solution containing 0.9% NaCl in water, where the solution volume will be such that the drug concentration is after release is less than 5% of saturation. The mixture is maintained at 37° C. and stirred slowly to maintain the implants in suspension. The appearance of the dissolved drug as a function of time may be followed by various methods known in the art, such as spectrophotometrically, HPLC, mass spectroscopy, etc. until the absorbance becomes constant or until greater than 90% of the drug has been released.

In addition to the alpha-2 adrenergic receptor agonist or alpha-2 adrenergic receptor agonists included in the intraocular implants disclosed herein, the intraocular implants may also include one or more additional ophthalmically acceptable therapeutic agents. For example, the implant may include one or more antihistamines, one or more antibiotics, one or more beta blockers, one or more steroids, one or more antineoplastic agents, one or more immunosuppressive agents, one or more antiviral agents, one or more antioxidant agents, and mixtures thereof.

Pharmacologic or therapeutic agents which may find use in the present systems, include, without limitation, those disclosed in U.S. Pat. No. 4,474,451, columns 4-6 and U.S. Pat. No. 4,327,725, columns 7-8.

Examples of antihistamines include, and are not limited to, loratadine, hydroxyzine, diphenhydramine, chlorpheniramine, brompheniramine, cyproheptadine, terfenadine, clemastine, triprolidine, carbinoxamine, diphenylpyraline, phenindamine, azatadine, tripelennamine, dexchlorpheniramine, dexbrompheniramine, methdilazine, and trimeprazine doxylamine, pheniramine, pyrilamine, chlorcyclizine, thonzylamine, and derivatives thereof.

Examples of antibiotics include without limitation, cefazolin, cephradine, cefaclor, cephapirin, ceftizoxime, cefoperazone, cefotetan, cefutoxime, cefotaxime, cefadroxil, ceftazidime, cephalexin, cephalothin, cefamandole, cefoxitin, cefonicid, ceforanide, ceftriaxone, cefadroxil, cephradine, cefuroxime, ampicillin, amoxicillin, cyclacillin, ampicillin, penicillin G, penicillin V potassium, piperacillin, oxacillin, bacampicillin, cloxacillin, ticarcillin, azlocillin, carbenicillin, methicillin, nafcillin, erythromycin, tetracycline, doxycycline, minocycline, aztreonam, chloramphenicol, ciprofloxacin hydrochloride, clindamycin, metronidazole, gentamicin, lincomycin, tobramycin, vancomycin, polymyxin B sulfate, colistimethate, colistin, azithromycin, augmentin, sulfamethoxazole, trimethoprim, and derivatives thereof.

Examples of beta blockers include acebutolol, atenolol, labetalol, metoprolol, propranolol, timolol, and derivatives thereof.

Examples of steroids include corticosteroids, such as cortisone, prednisolone, fluorometholone, dexamethasone, medrysone, loteprednol, fluazacort, hydrocortisone, prednisone, betamethasone, prednisone, methylprednisolone, triamcinolone hexacetonide, paramethasone acetate, diflorasone, fluocinonide, fluocinolone, triamcinolone, derivatives thereof, and mixtures thereof.

Examples of antineoplastic agents include adriamycin, cyclophosphamide, actinomycin, bleomycin, daunorubicin, doxorubicin, epirubicin, mitomycin, methotrexate, fluorouracil, carboplatin, carmustine (BCNU), methyl-CCNU, cisplatin, etoposide, interferons, camptothecin and derivatives thereof, phenesterine, taxol and derivatives thereof, taxotere and derivatives thereof, vinblastine, vincristine, tamoxifen, etoposide, piposulfan, cyclophosphamide, and flutamide, and derivatives thereof.

Examples of immunosuppressive agents include cyclosporine, azathioprine, tacrolimus, and derivatives thereof.

Examples of antiviral agents include interferon gamma, zidovudine, amantadine hydrochloride, ribavirin, acyclovir, valacyclovir, dideoxycytidine, phosphonoformic acid, ganciclovir, and derivatives thereof.

Examples of antioxidant agents include ascorbate, alpha-tocopherol, mannitol, reduced glutathione, various carotenoids, cysteine, uric acid, taurine, tyrosine, superoxide dismutase, lutein, zeaxanthin, cryptoxanthin, astaxanthin, lycopene, N-acetyl-cysteine, carnosine, gamma-glutamyl-cysteine, quercetin, lactoferrin, dihydrolipoic acid, citrate, Ginkgo Biloba extract, tea catechins, bilberry extract, vitamins E or esters of vitamin E, retinyl palmitate, and derivatives thereof.

Other therapeutic agents include squalamine, carbonic anhydrase inhibitors, alpha agonists, prostamides, prostaglandins, antiparasitics, antifungals, and derivatives thereof.

The amount of active agent or agents employed in the implant, individually or in combination, will vary widely depending on the effective dosage required and the desired rate of release from the implant. Usually the agent will be at least about 1, more usually at least about 10 weight percent of the implant, and usually not more than about 80, more usually not more than about 40 weight percent of the implant.

In addition to the therapeutic component, the intraocular implants disclosed herein may include effective amounts of buffering agents, preservatives and the like. Suitable water soluble buffering agents include, without limitation, alkali and alkaline earth carbonates, phosphates, bicarbonates, citrates, borates, acetates, succinates and the like, such as sodium phosphate, citrate, borate, acetate, bicarbonate, carbonate and the like. These agents advantageously present in amounts sufficient to maintain a pH of the system of between about 2 to about 9 and more preferably about 4 to about 8. As such the buffering agent may be as much as about 5% by weight of the total implant. Suitable water soluble preservatives include sodium bisulfite, sodium bisulfate, sodium thiosulfate, ascorbate, benzalkonium chloride, chlorobutanol, thimerosal, phenylmercuric acetate, phenylmercuric borate, phenylmercuric nitrate, parabens, methylparaben, polyvinyl alcohol, benzyl alcohol, phenylethanol and the like and mixtures thereof. These agents may be present in amounts from 0.001 to about 5% by weight and preferably 0.01 to about 2% by weight. In at least one of the present implants, a purite preservative is provided in the implant, such as when the alpha-2 adrenergic receptor agonist is brimonidine. Thus, these implants may contain a therapeutically effective amount of Alphagan-P®.

In some situations mixtures of implants may be utilized employing the same or different pharmacological agents. In this way, a cocktail of release profiles, giving a biphasic or triphasic release with a single administration is achieved, where the pattern of release may be greatly varied.

Additionally, release modulators such as those described in U.S. Pat. No. 5,869,079 may be included in the implants. The amount of release modulator employed will be dependent on the desired release profile, the activity of the modulator, and on the release profile of the alpha-2 adrenergic receptor agonist in the absence of modulator. Electrolytes such as sodium chloride and potassium chloride may also be included in the implant. Where the buffering agent or enhancer is hydrophilic, it may also act as a release accelerator. Hydrophilic additives act to increase the release rates through faster dissolution of the material surrounding the drug particles, which increases the surface area of the drug exposed, thereby increasing the rate of drug bioerosion. Similarly, a hydrophobic buffering agent or enhancer dissolve more slowly, slowing the exposure of drug particles, and thereby slowing the rate of drug bioerosion.

In certain implants, an implant (or a plurality of up to six implants) comprising brimonidine or brimonidine tartrate and a biodegradable polymer matrix is able to release or deliver an amount of brimonidine between about 0.1 mg to about 2.4 mg for about 3-6 months after implantation into the eye. The implant may be configured as a rod, bar, disc or wafer. A rod-shaped implant may be derived from filaments extruded from a 720 μm nozzle and cut into 1 mg size. A wafer-shaped implant may be a circular disc having a diameter of about 2.5 mm, a thickness of about 0.127 mm, and a weight of about 1 mg.

The proposed 3-month release formulations may be sterile, and bioerodible in the form of a rod, a wafer or a microsphere containing brimonidine tartrate within a PLA matrix or POE matrix. The implants are designed to delay the clearance of the drug and reduce the need for repeated implantation over 3-month period, thereby lowering the risk of complications.

Various techniques may be employed to produce the implants described herein. Useful techniques include, but are not necessarily limited to, solvent evaporation methods, phase separation methods, interfacial methods, molding methods, injection molding methods, extrusion methods, co-extrusion methods, carver press method, die cutting methods, heat compression, combinations thereof and the like.

Specific methods are discussed in U.S. Pat. No. 4,997, 652. Extrusion methods may be used to avoid the need for solvents in manufacturing. When using extrusion methods, the polymer and drug are chosen so as to be stable at the temperatures required for manufacturing, usually at least about 85 degrees Celsius. Extrusion methods use temperatures of about 25 degrees C. to about 150 degrees C., more preferably about 65 degrees C. to about 130 degrees C. An implant may be produced by bringing the temperature to about 60 degrees C. to about 150 degrees C. for drug/polymer mixing, such as about 130 degrees C., for a time period of about 0 to 1 hour, 0 to 30 minutes, or 5-15 minutes.

For example, a time period may be about 10 minutes, preferably about 0 to 5 min. The implants are then extruded at a temperature of about 60 degrees C. to about 130 degrees C., such as about 75 degrees C.

In addition, the implant may be coextruded so that a coating is formed over a core region during the manufacture of the implant.

Compression methods may be used to make the implants, and typically yield implants with faster release rates than extrusion methods. Compression methods may use pressures of about 50-150 psi, more preferably about 70-80 psi, even more preferably about 76 psi, and use temperatures of about 0 degrees C. to about 115 degrees C., more preferably about 25 degrees C.

The implants of the present invention may be inserted into the eye, for example the vitreous chamber of the eye, by a variety of methods, including placement by forceps or by trocar following making a 2-3 mm incision in the sclera. One example of a device that may be used to insert the implants into an eye is disclosed in U.S. Patent Publication No. 2004/0054374. The method of placement may influence the therapeutic component or drug release kinetics. For example, delivering the implant with a trocar may result in placement of the implant deeper within the vitreous than placement by forceps, which may result in the implant being closer to the edge of the vitreous. The location of the implant may influence the concentration gradients of therapeutic component or drug surrounding the element, and thus influence the release rates (e.g., an element placed closer to the edge of the vitreous may result in a slower release rate).

The present implants are configured to release an amount of alpha-2 adrenergic receptor agonist in an eye for a period of time to minimize an ocular vascular occlusion, such as a retinal vascular occlusion. Retinal vascular occlusion may result from a variety of diseases such as retinal arterial occlusive disease, central retinal vein occlusion, disseminated intravascular coagulopathy, branch retinal vein occlusion, hypertensive fundus changes, ocular ischemic syndrome, retinal arterial microaneurysms, hemi-retinal vein occlusion, central retinal artery occlusion, branch retinal artery occlusion, carotid artery disease (cad), eales disease and vasculopathies associated with diabetes. By implanting the alpha-2 adrenergic receptor agonist-containing implants into the vitreous of an eye, it is believed that the agonist is effective to reduce occlusion within blood vessels located in the eye.

In addition, the present implants may be configured to release an alpha-2 adrenergic receptor agonist in a therapeutically effective amount for a period of time effective to treat glaucoma of a patient.

The implants disclosed herein may also be configured to release additional therapeutic agents, as described above, which may be effective in treating diseases or conditions, such as the following:

Maculopathies/retinal degeneration: macular degeneration, including age related macular degeneration (ARMD), such as non-exudative age related macular degeneration and exudative age related macular degeneration, choroidal neovascularization, retinopathy, including diabetic retinopathy, acute and chronic macular neuroretinopathy, central serous chorioretinopathy, and macular edema, including cystoid macular edema, and diabetic macular edema. Uveitis/retinitis/choroiditis: acute multifocal placoid pigment epitheliopathy, Behcet's disease, birdshot retinochoroidopathy, infectious (syphilis, lyme, tuberculosis, toxoplasmosis), uveitis, including intermediate uveitis (pars planitis) and anterior uveitis, multifocal choroiditis, multiple evanescent white dot syndrome (MEWDS), ocular sarcoidosis, posterior scleritis, serpignous choroiditis, subretinal fibrosis, uveitis syndrome, and Vogt-Koyanagi-Harada syndrome. Vascular diseases/exudative diseases: retinal arterial occlusive disease, central retinal vein occlusion, disseminated intravascular coagulopathy, branch retinal vein occlusion, hypertensive fundus changes, ocular ischemic syndrome, retinal arterial microaneurysms, Coat's disease, parafoveal telangiectasia, hemi-retinal vein occlusion, papillophlebitis, central retinal artery occlusion, branch retinal artery occlusion, carotid artery disease (CAD), frosted branch angiitis, sickle cell retinopathy and other hemoglobinopathies, angioid streaks, familial exudative vitreoretinopathy, Eales disease. Traumatic/surgical: sympathetic ophthalmia, uveitic retinal disease, retinal detachment, trauma, laser, PDT, photocoagulation, hypoperfusion during surgery, radiation retinopathy, bone marrow transplant retinopathy. Proliferative disorders: proliferative vitreal retinopathy and epiretinal membranes, proliferative diabetic retinopathy. Infectious disorders: ocular histoplasmosis, ocular toxocariasis, presumed ocular histoplasmosis syndrome (PONS), endophthalmitis, toxoplasmosis, retinal diseases associated with HIV infection, choroidal disease associated with HIV infection, uveitic disease associated with HIV Infection, viral retinitis, acute retinal necrosis, progressive outer retinal necrosis, fungal retinal diseases, ocular syphilis, ocular tuberculosis, diffuse unilateral subacute neuroretinitis, and myiasis. Genetic disorders: retinitis pigmentosa, systemic disorders with associated retinal dystrophies, congenital stationary night blindness, cone dystrophies, Stargardt's disease and fundus flavimaculatus, Bests disease, pattern dystrophy of the retinal pigmented epithelium, X-linked retinoschisis, Sorsby's fundus dystrophy, benign concentric maculopathy, Bietti's crystalline dystrophy, pseudoxanthoma elasticum. Retinal tears/holes: retinal detachment, macular hole, giant retinal tear. Tumors: retinal disease associated with tumors, congenital hypertrophy of the RPE, posterior uveal melanoma, choroidal hemangioma, choroidal osteoma, choroidal metastasis, combined hamartoma of the retina and retinal pigmented epithelium, retinoblastoma, vasoproliferative tumors of the ocular fundus, retinal astrocytoma, intraocular lymphoid tumors. Miscellaneous: punctate inner choroidopathy, acute posterior multifocal placoid pigment epitheliopathy, myopic retinal degeneration, acute retinal pigment epithelitis and the like.

In one embodiment, an implant, such as the implants disclosed herein, is administered to a posterior segment of an eye of a human or animal patient, and preferably, a living human or animal. In at least one embodiment, an implant is administered without accessing the subretinal space of the eye. For example, a method of treating a patient may include placing the implant directly into the posterior chamber of the eye. In other embodiments, a method of treating a patient may comprise administering an implant to the patient by at least one of intravitreal injection, subconjunctival injection, sub-tenon injections, retrobulbar injection, and suprachoroidal injection.

In at least one embodiment, a method of reducing retinal vascular occlusion in a patient comprises administering one or more implants containing one or more alpha-2 adrenergic receptor agonists, as disclosed herein to a patient by at least one of intravitreal injection, subconjunctival injection, sub-tenon injection, retrobulbar injection, and suprachoroidal injection. A syringe apparatus including an appropriately sized needle, for example, a 27 gauge needle or a 30 gauge needle, can be effectively used to inject the composition with the posterior segment of an eye of a human or animal.

Repeat injections are often not necessary due to the extended release of the alpha-2 adrenergic receptor agonists from the implants.

In another aspect of the invention, kits for treating an ocular condition of the eye are provided, comprising: a) a container comprising an extended release implant comprising a therapeutic component including an alpha-2 adrenergic receptor agonist, such as brimonidine free base or brimonidine tartrate (e.g., Alphagan-P), and a drug release sustaining component; and b) instructions for use. Instructions may include steps of how to handle the implants, how to insert the implants into an ocular region, and what to expect from using the implants.

EXAMPLES

The following examples illustrate embodiments of our invention. We developed the formulations set forth in the Examples below with considerably difficultly. Thus, over a hundred formulations were tested before arriving at the specific useful formulation set forth in the Examples below. We determined that with drug (i.e. brimonidine) loads greater than about 35 weight %, high burst and subsequent poor drug release profile ensures. Thus, we determined that many formulations of brimonidine free base (BFB) presented in vitro a lag release period while many brimonidine tartrate (BT) formulations showed an initial burst release. Additionally, we determined that many 50:50 (BT:BFB) formulations displayed burst and a late-stage poor (very slow or minimal rate of) drug release.

However, we persevered and discovered that specific BT, BFB, and polymer (PLA and PLGA) combinations achieved desirable release profiles, as shown in FIG. 1. We determined that addition of low molecular weight acid end-capped poly (D,L-lactide-co-glycolide) polymer (RG502H) and a lower proportion of BT were important to obtaining the desired release characteristics and that presence in the formulations of only the two ester end-capped poly (D,L-lactide) polymer (R203s and R208) did not show the desired release profile. Hence, a particular hydrophilic to hydrophobic polymer balance was important in order to achieve the correct release profile.

Previously it was thought that use of low molecular weight (molecular weight less than about 20,000 Daltons and preferably less than all 15,000 Daltons) hydrophilic polymer would cause the extruded drug-implant made to have a significantly initial burst release. Contrarily we determined, for example, that use of particular amounts, ratios and proportions of the low molecular weight polymers: ester end-capped poly (D,L-lactide) in combination with two ester end-capped poly (D,L-lactide) polymers (i.e. R203s and R208) resulted in a desirable linear and non-burst release profile.

Example 1

High-Load Brimonidine Implant with Improved Release Profile

As previously set forth it is known that topical application of the alpha-2 adrenergic receptor agonist brimonidine is effective when topically administered to treat open-angle glaucoma and ocular hypertension. Brimonidine also has neuroprotective and visual acuity enhancing properties when given intravitreally. We determined that a sustained release polymer implant can effectively deliver a therapeutic dose of brimonidine over an extended period of time in the Tenon's capsule (i.e. into the sub-tenon space) and/or into the vitreous for treating, respectively, an anterior or a posterior ocular condition. It is highly advantageous for an implant to carry (i.e. by loaded with) as much active drug as possible so as to increase (upon regular, period release of the therapeutic agent from the administered implant) the duration of therapeutic drug dosing. In this Example, we surprisingly determined that use of brimonidine free base (BFB) instead of brimonidine tartrate (BT) enables an implant constituted of particular bioerodible polymers to carry 51% more moles of BFB as opposed to BT for an equal weight implant comprising the same polymers and made by the same process. BFB however is not as water soluble as is BT (the tartrate salt of brimonidine) so there can be a substantial lag time in the BFB release profile upon administration of the implant. Additionally, implants with higher loads of BT often show a "burst" release (as compared to BFB) because of BT's high solubility. Hence, we additionally developed new formulations with particular polymers which, as well as permitting significantly higher BFB drug loads (as compared to the wt % drug load possible with BT as the drug) also exhibit substantially linear release profiles of the brimonidine free-base from the particular polymers new formulation sustained release polymer implants we discovered from the infinite combinations of possible polymers.

Specifically, we developed a high-load brimonidine free-base containing sustained release polymer implant with an improved release profile that does not show an initial "burst" or a "lag" period and our new formulation contains brimonidine free base (BFB) dispersed in a biodegradable polymer matrix. In this Example, the polymer matrix consisted of two poly (D,L-lactide) (PLA) polymers and one poly (D,L-lactide-co-glycolide) (PLGA) polymer. Brimonidine free base is poorly water soluble and makes the implant more hydrophobic so typically upon implantation initial water permeation is delayed and consequently so is the release of BFB and a "lag" is observed. Surprisingly, the high-load implant we developed contains as much as 60 weight % BFB and yet shows a nearly linear release profile without a burst or lag period.

As an embodiment within the scope of our invention we made heat extruded implants (formulation R-2007-8933-028) containing 50 wt % (high load) BFB, 20 wt % R2035 (a PLA polymer), 20 wt % R208 (also a PLA polymer), and 10 wt % RG502H (a PLGA polymer). Another embodiment of our invention was a heat extruded implant (formulation R-2007-8933-060) comprising 60 wt % (very high load) BFB, 16 wt % R203S, 16 wt % R208, and 8 wt % RG502H. Polymers were used as received from Boehringer Ingelheim (Resomer®). Brimonidine free base and brimonidine tartrate were obtained from Ash Stevens, Inc. (Riverview, Mich.).

The polymer implants in this experiment were made by melt (heat) extrusion using a twin-screw microcompounder/extruder (such as that made by DSM), but they can also be made by direct compression or by solvent casting. The implants made were bar-shaped (with average dimensions of 1.0 mm×0.5 mm), but they can be made into any geometric shape by changing the extrusion or compression die.

The polymers selected and BFB were combined in a stainless steel container containing two 10-mm stainless steel balls and blended in a Turbula mixer for 15 minutes. The container was removed from the mixer and the powder blend was stirred with a spatula. The powder blend was inspected for homogeneity and the mixing procedure was repeated.

The DSM twin-screw microcompounder/extruder was setup according to the manufacturer's instructions. The output of the extruder was fitted with a laser micrometer and a puller to control the thickness of the extruded bar. The DSM twin-screw microcompounder/extruder was allowed to equilibrate to the extrusion temperature (between 85° and 110° C.), then the powder blend was manually fed into the extrusion screws at a rate of 2 grams/minute, which rate maintained a constant load and torque.

The extruded filaments were then cut into two-milligram bars (approximately 3-mm long) and their drug release monitored in phosphate buffered saline (pH 7.4, 0.01 M) by HPLC. The in vitro release data obtained from sample formulations made in this Example 1 are shown in FIG. 1. Other series of formulations, with 60% loading of BFB, but with a different polymer ratio showed this release rate effect as well. Examples of the formulations made are summarized in Table 1.

TABLE 1

Brimonidine Free Base Containing Formulations

| Formulation No | Weight % | | | |
|---|---|---|---|---|
| | Brimonidine Free Base | Resomer R203S[1] | Resomer R208[1] | Resomer RG502H[2] |
| R-2007-8933-027 | 35 | 35 | 20 | 10 |
| R-2007-8933-028 | 50 | 20 | 20 | 10 |
| R-2007-8933-060 | 60 | 16 | 16 | 8 |

[1]Ester end-capped poly (D,L-lactide) polymer
[2]Ester end-capped poly (D,L-lactide-co-glycolide) polymer This experiment surprisingly showed that high load BFB implants can be made with substantially linear release rate (i.e. straight line release over time) as shown for example over days 5 to 50 for the 60 wt % BFB FIG. 1 implant.

Example 2

Brimonidine Implant with Linear Release Kinetics

Brimonidine tartrate is more water soluble than brimonidine free base so implants containing BT often show a "burst" release because of the availability of surface brimonidine tartrate. On the other hand, brimonidine free base is not water soluble and makes the implant more hydrophobic. In this case, initial water permeation is delayed and consequently so is the release of brimonidine, which is observed as a "lag" in the BFB release profile.

In this experiment we discovered implants formulations with more substantially linear release rates than was obtained with the Example 1 implants, and as well without significant either burst or lag brimonidine release observed from the implant. Thus we developed these new Example 3 formulations as combinations of brimonidine free base (BFB) and brimonidine tartrate (BT) dispersed in a biodegradable matrix comprising several different polymers. In this example, the most preferred formulation (R-2007-8933-035) consisted of a polymer matrix which was a mixture of two different ester end-capped PLAs and one acid end-capped PLA as well as BFB and BT. So in this Example we developed sustained release drug-delivery formulations that is structurally stable and provides zero order (linear) release kinetics without an initial burst effect or lag. The formulations made are summarized in Table 2 and the release profiles are shown in FIG. 2.

RG502H is (50:50) poly(D,L-lactide-co-glycolide), RG752s is (75:25) poly(D,L-lactide-co-glycolide), R202H is 100% poly(D,L-lactide) with acid end group or terminal acid groups, R203 and R206 are both 100% poly(D,L-lactide). The inherent viscosity of RG502, RG752, R202H, R203, and R206 0.2, 0.2, 0.2, 0.3 and 1.0 dL/g, respectively. The inherent viscosity of both RG502H and RG752s is between 0.16 and 0.24 dl/g. The inherent viscosity of R203s is between 0.25 and 0.35 dl/g. The average molecular weight of RG502, RG752, R202H, R203, and R206 are 11700, 11200, 6500, 14000, and 63300 Daltons, respectively.

TABLE 2

BT and BFB Containing Formulations

| Formulation No | Weight % | | | | | |
|---|---|---|---|---|---|---|
| | Brimonidine Free Base | Brimonidine Tartrate | Resomer R203S[1] | Resomer R208[1] | Resomer RG502H[2] | Resomer R202H[3] |
| R-2007-8933-032 | 25 | 10 | 35 | 20 | 10 | 0 |
| R-2007-8933-033 | 40 | 10 | 20 | 20 | 10 | 0 |
| R-2007-8933-034 | 25 | 10 | 35 | 20 | 0 | 10 |
| R-2007-8933-035 | 40 | 10 | 20 | 20 | 0 | 10 |

[1]Ester end-capped poly (D,L,-lactide) polymer
[2]Acid end-capped poly (D,L,-lactide-co-glycolide) polymer
[3]Acid end-capped poly (D,L,-lactide) polymer The Example 2 formulations made contained brimonidine free base, brimonidine tartrate, two hydrophobic, ester end-capped poly (D,L-lactide) polymers (PLA), and an acid end-capped poly (D,L-lactide-co-glycolide) polymer (PLGA). One formulation (R-2007-8933-035) contained 40% BFB, 10% BT, 20% R203S (a PLA), 20% R208 (a second PLA), and 10% R202H (also a third PLA) and exhibited near perfect linear release kinetics, the dotted line in FIG. 2 representing perfect linear release. FIG. 2 additionally shows a comparison of the Example 2 new formulation three polymer formulations made with and an Example 1 high load BFB implant. Other formulations we made with the same BFB:BT ratio but with a different polymer ratio failed to show the same zero order release kinetics.

The implants were made using the same heat extrusion process set forth in Example 1 and in vivo release data was also obtained by the method set forth in Example 1.

Example 3

High-Load Extruded Bars and Injection-Molded Discs for Ocular Sustained Release Polymer Implants In this experiment we made bar-shaped and disc-shaped sustained release polymer implants, which are inserted in vivo below the Tenon's capsule and above the sclera at a point posterior to the limbus of the eye for therapeutic purposes (to reduce IOP). We found that release of drug in vivo was controlled and maintained for long periods of time with little drug at sites anatomically distant from the intraocular site of administration.

The distinct (bar or disc) shape of the implants made in this Example maximized the contact surface area of implant to the episcleral (intrascleral) region, which is desirable for this diffusion-based implant system. We also found that having rounded edges on the long axis of the bar-shaped implants reduced the potential for overlying conjunctival erosions and the potential for implant extrusion from the site of administration, as compared to rod or filament shaped implants which have a cylindrical shape. Advantageously, these low-profile, flat (bar or disc) implants, place the long axis of the implant parallel to the limbus in the sub-Tenon's space. These implant can also be injected, which is an important advantage over surgically implanted implants. A bar shaped implant (vs rod-shaped) is also less likely to roll with the blinking action and this gives such an implant greater stability and less foreign body sensation for the patient. Lastly, given that the bar implant has two distinct flat sides; one side can be coated with a polymer that may reduce the diffusion of drug towards the conjunctival side and encourages more drug-release towards the scleral side. Reducing the drug exposure to the conjunctiva is advantageous because the rich supply of lymphatic vessels in the conjunctiva bilayer is very efficient at clearing drugs from the sub-Tenon's space, and, consequently, reducing the drug exposure to the target tissue (i.e., the ciliary body region).

The disc implant's shape, have a preferred height of less than or equal to 1.0 mm, but preferably less than or equal to 0.5 mm, which can reduce the potential for conjunctival erosions. The disc-shaped implants have the advantages of holding a large amount of drug and a reduced tendency to erode from the sub-Tenon's space.

The bar-shaped implants in this study were made by melt extrusion in a twin-screw micro extruder, but they can also be made by direct compression or by solvent casting.

One example of a bar-shaped formulation made by melt extrusion (R-2007-8933-059) contained brimonidine free base (BFB) dispersed in a biodegradable polymer matrix with the in vivo release characteristics shown in FIG. 4. In this 059 formulation the polymer matrix consisted of two poly (D,L-lactide) PLA polymers and one poly (D,L,-lactide-co-glycolide) polymer. Other series of formulations, with 60% loading of BFB, but with a different polymer ratio showed this linear release effect as well. The BFB formulations made are summarized in Table 3.

TABLE 3

Brimonidine Free Base Containing Formulations

| Formulation No | Weight % | | | |
| --- | --- | --- | --- | --- |
| | Brimonidine Free Base | Resomer R203S[1] | Resomer R208[1] | Resomer RG502H[2] |
| R-2007-8933-027 | 35 | 35 | 20 | 10 |
| R-2007-8933-059 | 50 | 20 | 20 | 10 |
| R-2007-8933-060 | 60 | 16 | 16 | 8 |

[1]Ester end-capped poly (D,L,-lactide) polymer
[2]Acid end-capped poly (D,L,-lactide-co-glycolide) polymer The combined twin-screw micro extruder and injection molding system was used to make the disc shaped implants. The melt stream from the twin-screw micro extruder was directed through the die orifice where it immediately entered a heated transfer cylinder. As the melt filled the cylinder, the plunger was pushed out of the cylinder. Next the cylinder was placed in the molder cradle of the injection molding unit. A pneumatic ram pushed the plunger forcing the melt into the mold where it is cooled and solidified. The molded samples were recovered from the mold with a compressed air assist if required. The disc-shaped implants weighed approximately 3.5 milligram and their in vivo drug release was monitored in phosphate buffered saline pH 7.4 by HPLC.

FIG. 5 shows that the release profile of disc-shaped formulation made by injection molding. This formulation (R-2007-8933-064) contained 50% BFB, 18% R2035, 18% R208, 8% RG752s, and 6% PEG-3350. Other series of formulations, with similar loading of BFB, but with a different polymer ratio show this effect as well. The disc shaped formulations made are summarized in Table 4.

TABLE 4

Brimonidine Free Base Containing Formulations

| Formulation No | Weight % | | | | | | |
| --- | --- | --- | --- | --- | --- | --- | --- |
| | Brimonidine Free Base | Resomer R203S[1] | Resomer R208[1] | Resomer RG752s[2] | Resomer RG502H[2] | Resomer R202H[3] | PEG 3350 |
| R-2007-8933-064 | 50 | 18 | 18 | 8 | 0 | 0 | 6 |
| R-2007-8933-065 | 50 | 18 | 18 | 0 | 8 | 0 | 6 |
| R-2007-8933-066 | 50 | 18 | 18 | 0 | 0 | 8 | 6 |

[1]Ester end-capped poly (D,L,-lactide) polymer
[2]Acid end-capped poly (D,L,-lactide-co-glycolide) polymer
[3]Acid end-capped poly (D,L,-lactide) polymer Sub-Tenon's Implanted bar-shaped implants show IOP reduction in rabbits. Thus, four NZW rabbits were anesthetized and prepared for eye surgery. A lid speculum was placed and a conjunctival incision was made with Westcott scissors in the superotemporal quadrant. A sub-Tenon's pocket was made and four brimonidine tartrate bar implants (formulation number: R-2007-8931-008G, 60% drug, 20% R203s, 20% R208) (each containing 600 ug BT) were placed on the episclera. The conjunctiva was re-approximated using 9-0 vicryl suture. The eyes demonstrated a sustained IOP reduction over a number of weeks with the sub-Tenon's bar implants. The mean reduction of IOP (measured in % change from baseline) was 25% by 7 days. Thereafter, the IOP reduction ranged from 25 to 42% and returned to baseline by 8 weeks. The bar implants were well tolerated and the animals did not exhibit any discomfort. Clinical examination showed no signs of conjunctival erosion over the implants and no signs of extrusion of any implant. The percent IOP reduction over time is shown in FIG. 6.

Example 4

Treatment of Glaucoma with an Intraocular Implant Containing Brimonidine Associated with a Biodegradable Polymer Matrix A 68 year old female is diagnosed with elevated intraocular pressure levels, and diagnoses glaucoma. A 2 mg bar shaped implant containing 1,200 μg of brimonidine tartrate (formulation 8933-060 of Example 1) is placed in the vitreous of both of the woman's eyes using a trocar. Alternately, the implant can be administered to the sub tenon space. After about 2 days intraocular pressure has decrease 40-50% from baseline.

The embodiments of our invention in the Examples above have the advantages of: (1) providing a sustained release formulation of an alpha-2-selective adrenergic receptor agonist, such as brimonidine which can be administered (i.e. by intrascleral injection or implantation of a suitable implant) once every one to six months to provide regular dosing of the alpha-2-selective adrenergic receptor agonist therapeutic agent to the eye of a patient in need thereof to thereby treat an ocular condition such as the elevated intraocular pressure characteristic of glaucoma; (2) provide a sustained release formulation of an alpha-2-selective adrenergic receptor agonist, such as brimonidine, which can be administered (i.e. by intravitreal injection or implantation of a suitable implant) once every one to six months to provide regular dosing of the alpha-2-selective adrenergic receptor agonist therapeutic agent to the eye of a patient in need thereof to thereby treat an ocular condition such as neurodegeneration another retinal disorder or condition such as macular degeneration, macular edema or other retinopathy, and (3) provide an intraocular, sustained release formulation of an alpha-2 agonist for treating glaucoma which does not have or has reduced side effects of rapid drug wash out, ocular discomfort, conjunctival hyperemia (eye redness), stinging, pain, decreased tear production and function, decreased tear film stability, superficial punctate keratitis, squamous cell metaplasia, and changes in cell morphology.

All references, articles, publications and patents and patent applications cited herein are incorporated by reference in their entireties.

While this invention has been described with respect to various specific examples and embodiments, it is to be understood that the invention is not limited thereto and that it can be variously practiced within the scope of the following claims.

We claim:

1. A method for treating macular degeneration comprising the step of intraocular administration of a biodegradable intraocular implant comprising:
    (a) about 50 weight percent brimonidine, and;
    (b) a biodegradable polymer which is a mixture of;
        (i) an acid end capped polymer (D,L-lactide) polymer, and
        (ii) a poly (D,L-lactide-co-glycolide) polymer.
2. The method of claim 1, wherein the brimonidine is brimonidine free base.
3. The implant of claim 2, wherein the implant is an extruded rod.
4. The method of claim 1, wherein the macular degeneration is atrophic macular degeneration.
5. The method of claim 4, wherein the implant is administered intravitreally.

* * * * *